(12) United States Patent
Wu et al.

(10) Patent No.: US 8,013,112 B2
(45) Date of Patent: Sep. 6, 2011

(54) COMPOSITIONS COMPRISING HUMAN BRAIN NATRIURETIC PEPTIDE (BNP) FRAGMENTS

(75) Inventors: Huaiqin Wu, Libertyville, IL (US); Gangamani S. Beligere, Grayslake, IL (US); Reika L. Campbell, Glenview, IL (US)

(73) Assignee: Abbott Laboratories, Abbott Park, IL (US)

( * ) Notice: Subject to any disclaimer, the term of this patent is extended or adjusted under 35 U.S.C. 154(b) by 481 days.

(21) Appl. No.: 12/128,995

(22) Filed: May 29, 2008

(65) Prior Publication Data

US 2008/0248491 A1    Oct. 9, 2008

Related U.S. Application Data

(63) Continuation of application No. 11/517,618, filed on Sep. 7, 2006, now abandoned, and a continuation of application No. PCT/US2007/077677, filed on Sep. 7, 2007.

(51) Int. Cl.
*A61K 38/00* (2006.01)
*A61K 38/04* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl. .......... 530/300; 530/326; 530/327; 930/50
(58) Field of Classification Search .................. None
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,607,023 A | 8/1986 | Thibault et al. |
| 4,634,665 A | 1/1987 | Axel et al. |
| 4,816,397 A | 3/1989 | Boss et al. |
| 4,816,567 A | 3/1989 | Cabilly et al. |
| 4,968,615 A | 11/1990 | Koszinowski et al. |
| 5,114,923 A | 5/1992 | Seilhamer et al. |
| 5,168,062 A | 12/1992 | Stinski |
| 5,179,017 A | 1/1993 | Axel et al. |
| 5,468,646 A | 11/1995 | Mattingly et al. |
| 5,545,806 A | 8/1996 | Lonberg et al. |
| 5,674,710 A | 10/1997 | Seilhamer et al. |
| 6,090,382 A | 7/2000 | Salfeld et al. |
| 6,117,644 A | 9/2000 | DeBold |
| 6,124,430 A | 9/2000 | Mischak et al. |
| 6,162,902 A | 12/2000 | Mischak et al. |
| 6,376,207 B1 | 4/2002 | Mischak et al. |
| 6,461,828 B1 | 10/2002 | Stanton et al. |
| 6,677,124 B2 | 1/2004 | Tsuji et al. |
| 6,770,740 B1 | 8/2004 | Rice et al. |
| 7,341,838 B2 | 3/2008 | Buechler et al. |
| 7,351,586 B2 | 4/2008 | Friese et al. |
| 2003/0022235 A1 | 1/2003 | Dahlen et al. |
| 2003/0162710 A1 | 8/2003 | Sudoh et al. |
| 2003/0199000 A1 | 10/2003 | Valkirs et al. |
| 2004/0132013 A1 | 7/2004 | De Bold |
| 2004/0175379 A1 | 9/2004 | DeVries et al. |
| 2004/0180396 A1 | 9/2004 | Bergmann et al. |
| 2004/0209307 A1 | 10/2004 | Valkirs et al. |
| 2004/0219509 A1 | 11/2004 | Valkirs et al. |
| 2004/0243010 A1 | 12/2004 | Zoghbi et al. |
| 2004/0253655 A1 | 12/2004 | Tsuji et al. |
| 2005/0014287 A1 | 1/2005 | Friese et al. |
| 2005/0064511 A1 | 3/2005 | Buechler et al. |
| 2006/0121042 A1 | 6/2006 | Dall'Acqua et al. |
| 2006/0183154 A1 | 8/2006 | Shih et al. |

FOREIGN PATENT DOCUMENTS

| | | |
|---|---|---|
| EP | 0 384 176 | 8/1990 |
| EP | 0 418 308 | 3/1991 |
| EP | 0 542 255 | 5/1993 |
| EP | 0 914 344 | 5/1999 |
| EP | 1 016 867 | 7/2000 |
| EP | 1 030 177 | 8/2000 |
| JP | 3297392 | 12/1991 |
| JP | 2676114 | 11/1997 |
| WO | 2007/094460 | 11/2004 |
| WO | WO2004094459 A2 | 11/2004 |
| WO | WO2005116655 A2 | 12/2005 |
| WO | WO2006029369 A2 | 3/2006 |

OTHER PUBLICATIONS

Byrne MP, et al. Protein Science 4:2545-2558, 1995.*
Benesch RE, et al. J. Protein Chem. 10(5):503-510, 1991.*
Abbott AXYSM® System, BNP package insert, REF 8G82-20 Abbott Diagnostics Division, Feb. 2004.
Apple, et al., "Quality Specifications for B-Type Natriuretic Peptide Assays," Clin. Chem., 51(3):486-493 (2005).
Ausubel, et al., *Curr. Protocols in Molec. Biol.*, Section 2.10 (Terry Brown) and Section 6.3 (William W. Strauss)(1997).

(Continued)

*Primary Examiner* — Robert Landsman
(74) *Attorney, Agent, or Firm* — Audrey L. Bartnicki; Lisa V. Mueller, Polsinelli Shughart; Paul A. Jenny, Polsinelli Shughart

(57) ABSTRACT

The present invention relates among other things to a composition comprising at least two (2) human BNP fragments, wherein each of the human BNP fragments of the composition are cross-linked to at least one of the other human BNP fragments of the composition.

10 Claims, 21 Drawing Sheets

OTHER PUBLICATIONS

Belenky, et al., "The effect of class-specific protease inhibitors on the stabilization of B-type natriuretic peptide in human plasma," *Clinica Chimica Acta*, 340:163-172 (2004).

Benjamini, et al., S., *Immunology, A Short Course*, Immunogens and Antigens, 2$^{nd}$ Ed., pp. 37-40 (1991).

Berzofsky, et al., "Antigen-Antibody Interactions and Monoclonal Antibodies," *Fund. Immunol.*, 2:315-336 (1989).

Bird, et al., "Single-Chain Antigen-Binding Proteins," *Science*, 242:423-426 (1988).

Bluestein, "Comparing BNP Assays, Factors Impacting Analytical Method Comparison," *Bayer Healthcare Diagnostics Division Publ.*, (2004).

Boder, et al., "Directed evolution of antibody fragments with monovalent femtomolar antigen-binding affinity," *PNAS*, 97(20): 10701-10705, (2000).

Boder, et al., "Optimal Screening of Surface-Displayed Polypeptide Libraries," *Biotechnol. Prog.*, 14:55-62 (1998).

Boder, et al., "Yeast Surface Display for Directed Evolution of Protein Expression, Affinity, and Stability," *Meth. In Enzymol.*, 328:430-444 (2000).

Boder, et al., "Yeast surface display for screening combinatorial polypeptide libraries," *Nature Biotech.*, 15(6):553-557 (1997).

Bogan, et al., "Anatomy of Hot Spots in Protein Interfaces," *J. Mol. Biol.*, 280:1-9 (1998).

Boss, et al., "Genetically engineered antibodies," *Imunol. Today*, 6(1):12-13 (1985).

Brandt, et al., "Dipeptidyl-Peptidase IV Converts Intact B-Type Natriuretic Peptide into Its *des*-SerPro Form," *Clin. Chem.*, 52(1):82-87 (2006).

Buckley, et al., "Cardiac peptide stability, aprotinin and room temperature: importance for assessing cardiac function in clinical practice," *Clin. Sci.*, 97:689-695 (1999).

Cataliotti, et al., "Circulating Natriuretic Peptide Concentrations in Patients with End-Stage Renal Disease: Role of Brain Natriuretic Peptide as a Biomarker for Ventricular Remodeling," *Mayo Clin. Proc.*, 76:1111-1119 (2001).

Davidson, et al., "Brain natriuretic peptide," *J. of Hypertension*, 12:329-336 (1994).

Diagnostic Automation/Cortez Diagnostics, Inc., "Nt-proBNP ELISA Quantitative dertermination of Nt-proBNP in biological fluids," (Cat. No. 2852-7), pp. 1-8 (1997).

Galfre, et al., "Antibodies to major histocompatibility antigens produced by hybrid cell lines," *Nature*, 266:550-552 (1977).

Gutkowska, et al., "Atrial Natriuretic Factor in Human Plasma," *Biochem. & Biophys. Res. Comm.*, 139(1):287-295 (1986).

Holmes, et al., "Renal, Endocrine, and Hemodynamic Effects of Human Brain Natriuretic Peptide in Normal Man," *J. of Clin. Endocrin. & Metab.*, 76(1):91-96 (1993).

Huston, et al., "Protein engineering of antibody binding sites: Recovery of specific activity in an anti-digoxin single-chain Fv analogue produced in *Escherichia coli*," *PNAS*, 85:5879-5883 (1988).

Itoh, et al., "Preparation of Monoclonal Antibodies against Brain Natriuretic Peptide and Their Application to Radioimmunoassay and Passive Immunization," *Endocrinology*, 127(3):1292-1300 (1990).

Kaufman, et al, "Amplification and Expression of Sequences cotransfected with a Modular Dihydrofolate Reductase Complementary DNA Gene," *J. Mol. Biol.*, 159:601-621 (1982).

Kenny, et al., "Hydrolysis of human and pig brain natriuretic peptides, urodilatin, C-type natriuretic peptide and some C-receptor ligands by endopeptidase-24.11," *Biochem. J.*, 291:83-88 (1993).

Ma, et al., "Protein-protein interactions: Structurally conserved residues distinguish between binding sites and exposed protein surfaces," *PNAS*, 100(10):5772-5777 (2003).

McCafferty, et al., "Phage antibodies: filamentous phage displaying antibody variable domains," *Nature*, 348:552-554 (1990).

Mizushima, et al., "pEF-BOS, a powerful mammalian expression vector," *Nucl. Acids Res.*, 18(17):5322 (1990).

Morrison, et al., "Chimeric human antibody molecules: Mouse antigen-binding domains with human constant region domains," *PNAS*, 81:6851-6855 (1984).

Motwani, et al., "Plasma brain natriuretic peptide as an indicator for angiotensin-converting—enzyme inhibition after myocardial infarction," *The Lancet*, 341:1109-1113 (1993).

Mukoyama, et al., "Brain Natriuretic Peptide as a Novel Cardiac Hormone in Humans," *J. Clin. Invest.*, 87:1402-1412 (1991).

Murdoch, et al., "Brain natriuretic peptide is stable in whole blood and can be measured using a simple rapid assay: implications for clinical practice," *Heart*, 78:594-597 (1997).

Nordin, et al., "Kinetic studies of small molecule interactions with protein kinases using biosensor technology," *Analytical Biochem.*, 340:359-368 (2005).

PCT International Application No. PCT/US07/77677, Transmittal of the International Search Report and the Written Opinion of the International Searching Authority, Mailed May 27, 2008.

Rajpal, et al., "A general method for greatly improving the affinity of antibodies by using combinatorial libraries," *PNAS*, 102(24):8466-8471 (2005).

Sanz, et al., "Comparison of BNP and NT-proBNP Assays in the Approach to the Emergency Diagnosis of Actue Dyspnea," *J. of Clin. Lab. Analysis*, 20:227-232 (2006).

Schiestl, et al., "High efficiency transformation of intact yeast cells using single stranded nucleic acids as a carrier," *Curr. Genet.*, 16:339-346 (1989).

Shimizu, et al., "Degradation of human brain natriuretic peptide (BNP) by contact activation of blood coagulation system," *Clinica Chimica Acta*, 305:181-186 (2001).

Shimizu, et al., "Molecular forms of human brain natriuretic peptide in plasma," *Clinica Chimica Acta*, 316:129-135 (2002).

Tetin, et al., "Interactions of Two Monclonal Antibodies with BNP: High Resolution Epitope Mapping Using Fluorescence Correlation Spectroscopy," *Biochem.*, 45:14155-14165 (2006).

Thorpe, et al., "Clonal Analysis of a Human Antimouse Antibody (HAMA) Response," *Scandinavian J. of Immunol.*, 57:85-92 (2003).

Urlaub, et al., "Isolation of Chinese hamster cell mutants deficient in dihydrofolate reductase activity," *PNAS*, 77(7):4216-4220 (1980).

Valli, et al., "Review of 10 years of the clinical use of brain natriuretic peptide in cardiology," *J. Lab. Clin. Med.*, 134(5):437-444 (1999).

Von Mehren, et al., "Monoclonal antibody-based therapy," *Current Opinion in Oncology*, 8:493-498, 1996.

Walther, et al., "Biochemical analysis of netural endopeptidase activity reveals independent catabolism of atrial and brain natriuretic peptide," *Biol. Chem.*, 385:179-184 (2004).

Watanabe, et al., "Prognostic Value of Plasma Brain Natriuretic Peptide Combined With Left Ventricular Dimensions in Predicting Sudden Death of Patients With Chronic Heart Failure," *J. of Cardiac Failure*, 11(1):50-55 (2005).

Yandle, "Biochemistry of natriuretic peptides," *J. of Int. Med.*, 235:561-576 (1994).

Yoshibayashi, et al., "Increased Plasma Levels of Brain Natriuretic Peptide in Hypertrophic Cardiomyopathy," *The New England J. of Med.*, 329(6):433-434 (1993).

Zahnd, et al., "Directed in Vitro Evolution and Crystallographic Analysis of a Peptide-binding Single Chain Antibody Fragment (scFv) with Low Picomolar Affinity," *J. of Biol. Chem.*, 279(18):18870-18877 (2004).

Beligere G., et al., "Evaluation of chemically and enzymatically prepared cross-linked BNP fragments", Biopolymers, 2007, 88(4), 551.

Supplementary European Search Report of EP Patent Application No. EP07841914, mailed Feb. 5, 2010, 7 pages total.

Kabat, et al., "Sequences of Proteins of Immun. Interest," U.S. Dept. of Health & Human Serv., NIH Publ. 91-3242, 5th: Tbl. of Cont. (1992) (Introduction and Table of Contents).

\* cited by examiner

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
        50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
                100             105
```

Figure 1

COMPOSITIONS COMPRISING HUMAN BRAIN NATRIURETIC PEPTIDE (BNP) FRAGMENTS

RELATED APPLICATION INFORMATION

This application is a continuation application of U.S. Ser. No. 11/517,618 filed Sep. 7, 2006 now abandoned, and is continuation application of International Application Number PCT/US2007/077677 filed Sep. 7, 2007 (pending), each of which are incorporated by reference in their entireties.

FIELD OF THE INVENTION

The present invention relates, among other things, to a composition comprising at least two (2) human BNP fragments, wherein each of the human BNP fragments of the composition are cross-linked to at least one of the other human BNP fragments of the composition. The present invention also relates to immunogens and antibodies produced using the immunogens. The present invention also further relates to immunoassays for detecting human BNP, human BNP fragments, compositions comprising at least two (2) human BNP fragments or combinations thereof, wherein each of the human BNP fragments of the compositions are cross-linked to at least one of the other human BNP fragments of the compositions.

BACKGROUND OF THE INVENTION

The following discussion of the background of the invention is merely provided to aid the reader in understanding the invention and is not admitted to describe or constitute prior art to the present invention.

Atrial natriuretic peptide (hereinafter referred to as "ANP"), brain natriuretic peptide (hereinafter referred to as "BNP"), C-type natriuretic peptide (hereinafter referred to as "CNP") and Dendroaspis natriuretic peptide (hereinafter referred to as "DNP") are each members of a family of hormones known as "natriuretic peptides". ANP and BNP share a wide spectrum of biological properties and belong to the cardiac natriuretic system. Both ANP and BNP are of myocardial cell origin while CNP is of endothelial cell origin. DNP was isolated from the venom of the green mamba snake and possesses structural similarity to ANP, BNP and CNP.

BNP received its name because it was first isolated from porcine brain, thus "BNP" stood for "brain natriuretic peptide". However, because BNP belongs to the cardiac natriuretic system, "brain" has been changed to "B-type". Therefore, "BNP" now refers to "B-type natriuretic peptide".

ANP is secreted by the heart in the atria. BNP is secreted by the heart through the coronary sinus, predominantly from the cardiac ventricles. BNP is secreted as a 108 amino acid polypeptide precursor (See, Valli et al., *J. Lab. Clin. Med.,* 134(5):437-444 (November 1999)). The mature form of BNP is made up of 32 amino acids (representing amino acids 77-108 of the 108 amino acid polypeptide precursor) with a 17 amino acid ring closed by a disulfide bond between two cysteine residues, an amino-terminal tail of 9 amino acids, and a carboxyl-terminal tail of 6 amino acids. ANP and CNP also have a 17 amino acid ring closed by a disulfide bond between two cysteine residues. Eleven of the seventeen amino acids in the ring are conserved between the three molecules. In addition to the 17 amino acid ring structure, ANP has an amino-terminal tail of 6 amino acids and a carboxy-terminal tail of 5 amino acids. ANP is produced as a 126 amino acid pro-ANP form that is the major storage form of ANP. After proteolytic cleavage between amino acids 98 and 99, the mature 28 amino acid peptide ANP is found in coronary sinus plasma (See, Yandle, *J. Internal Med.,* 235:561-576 (1994)).

CNP is found in the brain and cerebral spinal fluid and is the most prevalent of the three peptides in the central nervous system. Little if any CNP is present in the heart. Pro-CNP is a 103 amino acid peptide that is processed into either CNP-53 (amino acids 51 to 103) or CNP-22 (amino acids 82 to 103) that are the active peptides. In addition the 17 amino acid ring structure, CNP-22 has an amino-terminal tail of 5 amino acids and contains no carboxy-terminal tail. CNP-53 is identical to CNP-22 except for a 31 amino acid extension at the amino terminal end.

As mentioned previously, DNP was isolated from the venom of the green mamba snake. The mature form of DNP is made up of 38 amino acids. DNP-like immunoreactivity (DNP-LI) has been reported in human plasma and the plasma concentration of DNP-LI has been found to be elevated in patients with congestive heart failure (See, Cataliotti, et al., *Mayo Clin. Proc.,* 76:111-1119 (2001)). Additionally, it is also known that the infusion of synthetic DNP results in marked natriuresis and diuresis in association with increased plasma and urinary cyclic guanosine monophosphate. Id.

One of the problems with natural human natriuretic peptides is that they are unstable in plasma and serum. Specifically, enzymes, such as proteases, cleave these peptides. For example, proteases cleave BNP (natural and synthetic) at various locations along its amino acid chain. For example, protease cleavage is known to occur at the amino terminus of BNP between amino acids 2-3 (Shimizu et al., *Clinica Chimica Acta,* 316:129-135 (2002)) and at its carboxy terminus between amino acids 30-32. Moreover, endopeptidase cleavage of BNP is also known in the art (Davidson and Struthers, J. *Hypertension,* 12:329-336 (1994)).

The measurement of mature BNP (i.e., the 32 amino acid molecule (amino acids 77-108 of the precursor polypeptide of BNP)) in humans (hereinafter referred to as "hBNP"), in the general population has been found to reflect cardiac diseases, such as congestive heart failure, ischemic heart diseases, atrial fibrillation and renal dysfunction. In fact, elevated levels of BNP in human plasma have been reported in heart disease, following acute myocardial infarction and during symptomless or subclinical ventricular dysfunction (See, Mukoyama et al., *J. Clin. Invest.,* 87:11402-11412 (1991), Motwani et al., *Lancet,* 341:1109-1113 (1993), Yoshibayashi et al., *New Eng. J. Med.,* 327:434 (1992)). Increased circulating levels of ANP are seen in congestive heart failure, chronic renal failure and in severe hypertension. The presence of CNP in human plasma remains controversial with reports of its absence or presence as CNP-22 (See, Yandle, *J. Internal Med.,* 235:561-576 (1994)).

A ligand binding assay is an analytical technique for measuring concentrations of substances commonly referred to as ligands that react selectively with specific binding proteins. Immunoassays that measure the concentrations of antigens that react selectively with specific antibodies are an example of a class of ligand binding assays.

Ligand binding assays, such as immunoassays, for measuring human natriuretic peptides in plasma, particularly hBNP, are well-known in the art and are commercially available. These immunoassays require the use of at least one or two specific antibodies as well as at least one calibrator and, ideally, at least one control. In addition to the calibrators and controls, immunoassays require the use of at least one test sample. Test samples are normally biological samples derived from serum, plasma, whole blood or other bodily fluids (normally from a human patient). The levels of at least one human natriuretic peptide in the test sample is quantified in the immunoassay.

For example, U.S. Pat. No. 6,162,902 (hereinafter referred to as the "'902 patent") discloses isolated antibodies that are monospecifically reactive to epitopes 1-10, 5-13 and 15-25 of hBNP. More particularly, the '902 patent describes two isolated monoclonal antibodies. The first monoclonal antibody is produced by hybridoma cell line 106.3 (ATCC Accession No. HB 12044) and is monospecifically reactive to epitopes 5-13 of hBNP. The second monoclonal antibody is produced by hybridoma cell line 201.3 (ATCC Accession No. HB 12045) and is monospecifically reactive to epitopes 1-10 of hBNP. The '902 patent also describes the use of the above antibodies in immunoassays for the purpose of quantifying the amount of hBNP in a biological sample. U.S. Pat. No. 6,677,124 (hereinafter referred to as the "'124 patent") discloses a monoclonal antibody that binds to an epitope having the amino acid sequence of LYS-VAL-LEU-ARG-ARG-HIS (SEQ ID NO:3) that is found in the C-terminal region of hBNP, namely epitopes 27-32. More particularly, the '124 patent describes a monoclonal antibody produced by hybridoma cell line BC203 (FERM BP-3515). The '124 patent also describes immunoassays for hBNP using this monoclonal antibody.

As mentioned previously herein, one of the problems with human natriuretic peptides is that they are unstable in plasma and serum. Thereupon, the identification of new degradation products (namely, human BNP fragments) is needed to assist in the design of assays to capture and detect as much of these human BNP fragments as possible. Such assays would provide a more accurate measurement of human BNP fragments in test samples. Additionally, the identification of new degradations products would facilitate the design of immunogens that could be used to produce antibodies against the conserved fragments or regions of human BNP.

SUMMARY OF THE INVENTION

In one embodiment, the present invention relates to a composition that comprises at least two (2) human BNP fragments, preferably wherein each of the human BNP fragments of the composition are cross-linked to at least one of the other human BNP fragments of the composition.

Specifically, the composition preferably comprises a first human BNP fragment and a second human BNP fragment. The first human BNP fragment preferably has an amino acid sequence comprising amino acid residues a-32, b-31 or c-30 of human BNP, wherein a is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30; b is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28 and 29, and c is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27 and 28. The second human BNP fragment preferably has an amino acid sequence comprising amino acid residues a-32, b-31 or c-30 of human BNP, wherein a is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30, b is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28 and 29, and c is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27 and 28. Optionally, in the composition, at least one amino acid residue in the first human BNP fragment, at least one amino acid residue in the second human BNP fragment, or at least one amino acid residue in the first human BNP fragment and the second human BNP fragment can be modified, changed, substituted or altered to allow for cross-linking of the human BNP fragments by a cross-linking agent, a cross-linker, or a combination of a cross-linking agent and a cross-linker. Regardless of whether or not at least one amino acid residue in the first human BNP fragment, at least one amino acid residue in the second human BNP fragment, or at least one amino acid residue in the first human BNP fragment and the second human BNP fragment are modified, changed, substituted or altered, preferably the first human BNP fragment and the second human BNP fragment can be cross-linked by a cross-linking agent, a cross-linker or a combination of a cross-linking agent and a cross-linker. Some of the compositions of the present invention preferably exhibit an "X" like shape as illustrated in FIGS. 5, 11 and 13.

In another embodiment, the present invention relates to a composition that preferably comprises at least two (2) human BNP fragments, wherein (a) each of the human BNP fragments has an amino acid sequence that includes a portion or all of amino acids 10 to 26 of human BNP; and (b) each of the human BNP fragments of the composition are cross-linked to at least one of the other human BNP fragments of the composition.

Specifically, the composition preferably comprises a first human BNP fragment and a second human BNP fragment. The first human BNP fragment and the second human BNP fragment preferably each have an amino acid sequence comprising amino acids residues selected from the group consisting of 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 3-14, 3-13, 3-12, 3-11, 3-10, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 6-14, 6-13, 6-12, 6-11, 6-10, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 7-14, 7-13, 7-12, 7-11, 7-10, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 8-12, 8-11, 8-10, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 9-14, 9-13, 9-12, 9-11, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 10-14, 10-13, 10-12, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 11-14, 11-13, 12-32, 12-31, 12-30, 12-29, 12-28, 12-27, 12-26, 12-25, 12-24, 12-23, 12-22, 12-21, 12-20, 12-19, 12-18, 12-17, 12-16, 12-15, 12-14, 13-32, 13-31, 13-30, 13-29, 13-28, 13-27, 13-26, 13-25, 13-24, 13-23, 13-22, 13-21, 13-20, 13-19, 13-18, 13-17, 13-16, 13-15, 14-32, 14-31, 14-30, 14-29, 14-28, 14-27, 14-26, 14-25, 14-24, 14-23, 14-22, 14-21, 14-20, 14-19, 14-18, 14-17, 14-16, 15-32, 15-31, 15-30, 15-29, 15-28, 15-27, 15-26, 15-25, 15-24, 15-23, 15-22, 15-21, 15-20, 15-19, 15-18, 15-17, 16-32, 16-31, 16-30, 16-29, 16-28, 16-27, 16-26, 16-25, 16-24, 16-23, 16-22, 16-21, 16-20, 16-19, 16-18, 17-32, 17-31, 17-30, 17-29, 17-28, 17-27, 17-26, 17-25, 17-24, 17-23, 17-22, 17-21, 17-20, 17-19, 18-32, 18-31, 18-30, 18-29, 18-28, 18-27, 18-26, 18-25, 18-24, 18-23, 18-22, 18-21, 18-20, 19-32, 19-31, 19-30, 19-29, 19-28, 19-27, 19-26, 19-25, 19-24, 19-23, 19-22, 19-21, 20-32, 20-31, 20-30, 20-29, 20-28, 20-27, 20-26, 20-25, 20-24, 20-23, 20-22, 21-32, 21-31, 21-30, 21-29, 21-28, 21-27, 21-26, 21-25, 21-24, 21-23, 22-32, 22-31, 22-30, 22-29, 22-28, 22-27, 22-26, 22-25, 22-24, 23-32, 23-31, 23-30, 23-29, 23-28, 23-27, 23-26, 23-25, 24-32, 24-31, 24-30, 24-29, 24-28, 24-27, 24-26, 25-32, 25-31, 25-30, 26-29 and 26-28 of human BNP.

Optionally, in the composition, at least one amino acid residue in the first human BNP fragment, at least one amino acid residue in the second human BNP fragment, or at least one amino acid residue in the first human BNP fragment and the second human BNP fragment can be modified, changed, substituted or altered to allow for cross-linking of the human BNP fragments by a cross-linking agent, a cross-linker or a combination of a cross-linking agent and a cross-linker. Regardless of whether or not at least one amino acid residue in the first human BNP fragment, at least one amino acid residue in the second human BNP fragment or at least one amino acid residue in the first human BNP fragment and the second human BNP fragment are modified, changed, substituted or altered, preferably the first human BNP fragment and the second human BNP fragment can be cross-linked by a cross-linking agent, a cross-linker, or a combination of a cross-linking agent and a cross-linker.

More specifically, the above-described composition optionally comprises a first human BNP fragment having an amino acid sequence comprising amino acid residues selected from the group consisting of 1-13, 1-17, 3-13 and 3-17 of human BNP, and desirably a second human BNP fragment having an amino acid sequence comprising residues 18-30 or 18-32 of human BNP. In such a composition, preferably the first human BNP fragment and second human BNP fragment are cross-linked at a cysteine residue contained within the first human BNP fragment and the second human BNP fragment.

In another embodiment, the present invention relates to an immunogen that preferably comprises any of the above-described compositions.

In yet another embodiment, the present invention relates to an antibody produced by the above-described immunogen and preferably which is capable of immunospecifically binding to an epitope of human BNP.

In yet another embodiment, the present invention relates to an immunoassay for human BNP or a human BNP fragment, wherein the immunoassay preferably comprises the above-described antibody.

In still yet another embodiment, the present invention relates to an immunoassay for a human BNP (hereinafter "hBNP") composition, wherein the composition preferably comprises at least two (2) hBNP fragments, wherein each of the human BNP fragments of the composition optionally are cross-linked to at least one of the other human BNP fragments of the composition. The immunoassay preferably comprises the steps of:

(a) contacting at least one antibody (e.g., an antibody produced by the method of the invention) or a functionally active fragment thereof with a test sample suspected of containing or known to contain the hBNP composition to form an antibody-hBNP complex; and (b) detecting the formation of the antibody-hBNP complex.

Additionally, the above-described immunoassay can further optionally comprise the step of contacting the antibody-hBNP complex with at least one detection antibody or functionally active fragment thereof to form a capture antibody-hBNP detection antibody complex, wherein the detection antibody or functionally active fragment thereof desirably is conjugated to a detectable label.

Moreover, in the above-described immunoassay, preferably the immunoassay can relate the amount of the capture-hBNP-detection antibody complexes formed to the amount of the human BNP composition in the test sample, e.g., via use of a standard curve for the human BNP composition.

In still yet another embodiment, the present invention relates to an immunoassay for a hBNP composition, wherein the composition comprises at least two (2) hBNP fragments, preferably wherein each of the human BNP fragments of the composition are cross-linked to at least one of the other human BNP fragments of the composition. The immunoassay preferably comprises the steps of:

(a) immobilizing at least one capture antibody or functionally active fragment thereof that binds to the hBNP composition onto a solid phase to produce an immobilized first antibody;

(b) contacting the immobilized capture antibody with a test sample suspected of containing the hBNP composition to form an immobilized capture antibody-hBNP complex; and (c) contacting the capture antibody-hBNP complex with at least one detection antibody or a functionally active fragment thereof to form an immobilized capture antibody-hBNP-detection antibody complex, wherein the detection antibody or functionally active fragment thereof is conjugated to a detectable label.

Optionally the immunoassay comprises the further steps:

(d) removing the test sample and washing the immobilized capture antibody-hBNP-detection antibody complexes, if desired;

(e) optionally determining the amount of capture antibody-hBNP-detection antibody complexes formed in step (c); and (f) further optionally relating the amount of the capture antibody-hBNP-detection antibody complexes formed to the amount of the hBNP composition, e.g., via use of a standard curve for hBNP or hBNP fragment.

In the above-described immunoassay, the detection antibody preferably can be a monoclonal antibody or a functionally active fragment thereof. Additionally, the detectable label used in the above-described immunoassay desirably can be a radioactive label, an enzymatic label, a chemiluminescent label, a fluorescence label, a thermometric label, an immuno-polymerase chain reaction label, or another appropriate label.

In still yet another embodiment, the present invention relates to an immunoassay for a hBNP composition, wherein the composition comprises at least two (2) hBNP fragments, wherein each of the human BNP fragments of the composition are cross-linked to at least one of the other human BNP fragments of the composition. The immunoassay preferably comprises the steps of:

(a) immobilizing at least one capture antibody or functionally active fragment thereof that binds to the hBNP composition onto a solid phase to produce an immobilized first antibody;

(b) contacting the immobilized capture antibody with a test sample suspected of containing the hBNP composition to form an first immobilized antibody-hBNP complex; and (c) contacting the immobilized capture antibody with a hBNP peptide, hBNP fragment, or hBNP analogue thereof that has been conjugated to a detectable label to form an second immobilized antibody-hBNP complex.

Optionally the immunoassay comprises the further steps:

(d) determining the amount of detectable label in second immobilized antibody-hBNP complexes formed in step (c), if desired; and (e) optionally relating the amount of the second antibody-hBNP-antibody complexes formed to the amount of the hBNP composition, e.g., via use of a standard curve for hBNP or hBNP fragment.

In still yet another embodiment, the present invention relates to an immunoassay for a hBNP composition, wherein the composition comprises at least two (2) hBNP fragments, wherein each of the human BNP fragments of the composition are cross-linked to at least one of the other human BNP fragments of the composition, the immunoassay preferably comprising the steps of:

(a) immobilizing a hBNP peptide, hBNP fragment, or hBNP analogue thereof onto a solid phase to produce an immobilized hBNP peptide, hBNP fragment, or hBNP analogue thereof;

(b) contacting the immobilized hBNP peptide, hBNP fragment, or hBNP analogue thereof with a test sample suspected of containing the hBNP composition; and (c) contacting the immobilized hBNP peptide, hBNP fragment, or hBNP analogue thereof and the test sample suspected of containing the hBNP composition with at least one antibody or functionally active fragment thereof that has been conjugated to a detectable label to form an immobilized hBNP-antibody complex and a non-immobilized hBNP-antibody complex.

Optionally the immunoassay comprises the further steps:

(d) removing the non-immobilized hBNP-antibody complex, if desired;

(e) optionally determining the amount of immobilized hBNP-antibody complex formed in step (c); and (f) further optionally relating the amount of the immobilized hBNP-antibody complex formed to the amount of the hBNP composition, e.g., via use of a standard curve for hBNP or hBNP fragment.

The detectable label used in the above-described immunoassay can be a radioactive label, an enzymatic label, a chemiluminescent label, a fluorescence label, a thermometric label, an immuno-polymerase chain reaction label, or any other appropriate label.

In still yet another embodiment, the present invention relates to an immunoassay for a hBNP composition, wherein the composition preferably comprises at least two (2) hBNP fragments, wherein (a) each of the hBNP fragments has an amino acid sequence that desirably includes a portion or all of the amino acids 10 to 26 of hBNP; and (b) each of the human BNP fragments of the composition optimally are cross-linked to at least one of the other human BNP fragments of the composition. The immunoassay preferably comprises the steps of:

(a) contacting at least one antibody or functionally active fragment thereof with a test sample suspected of containing or known to contain the hBNP composition to form an antibody-hBNP complex; and (b) detecting the formation of the antibody-hBNP complex.

In the above-described immunoassay, the immunoassay can optionally further comprise the steps of contacting the antibody-hBNP complex with at least one detection antibody or functionally active fragment thereof to form a capture antibody-hBNP detection antibody complex, preferably wherein the detection antibody or functionally active fragment thereof is conjugated to a detectable label. The detectable label that can be used can be a radioactive label, an enzymatic label, a chemiluminescent label, a fluorescence label, a thermometric label, an immuno-polymerase chain reaction label, or any appropriate label. Moreover, in the above-described immunoassay, the immunoassay preferably can relate the amount of the capture-hBNP-detection antibody complexes formed to the amount of the human BNP composition in the test sample, e.g., via use of a standard curve for the human BNP composition.

In still yet another embodiment, the present invention relates to an immunoassay for a hBNP composition, wherein (a) each of the hBNP fragments preferably has an amino acid sequence that includes a portion or all of the amino acids 10 to 26 of hBNP; and (b) each of the human BNP fragments of the composition preferably are cross-linked to at least one of the other human BNP fragments of the composition. The immunoassay preferably comprises the steps of:

(a) immobilizing at least one capture antibody or functionally active fragment thereof that binds to the hBNP composition onto a solid phase to produce an immobilized first antibody;

(b) contacting the immobilized capture antibody with a test sample suspected of containing the hBNP composition to form an immobilized capture antibody-hBNP complex; and (c) contacting the capture antibody-hBNP complex with at least one detection antibody or a functionally active fragment thereof to form an immobilized capture antibody-hBNP-detection antibody complex, wherein the detection antibody or functionally active fragment thereof is conjugated to a detectable label.

Optionally the immunoassay comprises the further steps:

(d) removing the test sample and washing the immobilized capture antibody-hBNP-detection antibody complexes, if desired;

(e) optionally determining the amount of capture antibody-hBNP-detection antibody complexes formed in step (c); and (f) further optionally relating the amount of the capture antibody-hBNP-detection antibody complexes formed to the amount of the hBNP composition, e.g., via use of a standard curve for hBNP or hBNP fragment.

In the immunoassay, the detection antibody preferably can be a monoclonal antibody or a functionally active fragment thereof. Moreover, the detectable label used in the immunoassay optionally can be a radioactive label, an enzymatic label, a chemiluminescent label, a fluorescence label, a thermometric label, an immuno-polymerase chain reaction label, or any appropriate label.

In still yet another embodiment, the present invention relates to an immunoassay for a hBNP composition, wherein the composition comprises at least two (2) hBNP fragments, wherein (a) each of the hBNP fragments preferably has an amino acid sequence that includes a portion or all of the amino acids 10 to 26 of hBNP; and (b) each of the human BNP fragments of the composition desirably are cross-linked to at least one of the other human BNP fragments of the composition. The immunoassay preferably comprises the steps of:

(a) immobilizing at least one capture antibody or functionally active fragment thereof that binds to the hBNP composition onto a solid phase to produce an immobilized first antibody;

(b) contacting the immobilized capture antibody with a test sample suspected of containing the hBNP composition to form an first immobilized antibody-hBNP complex; and (c) contacting the immobilized capture antibody with a hBNP peptide, hBNP fragment, or hBNP analogue thereof that has been conjugated to a detectable label to form an second immobilized antibody-hBNP complex.

Optionally the immunoassay comprises the further steps:

(d) determining the amount of detectable label in second immobilized antibody-hBNP complexes formed in step (c), if desired; and (e) optionally relating the amount of the second antibody-hBNP-antibody complexes formed to the amount of the hBNP composition, e.g., via use of a standard curve for hBNP or hBNP fragment.

The detectable label used in the above-described immunoassay preferably can be a radioactive label, an enzymatic label, a chemiluminescent label, a fluorescence label, a thermometric label, an immuno-polymerase chain reaction label, or any appropriate label.

In yet still another embodiment, the present invention relates to an immunoassay for a hBNP composition, wherein (a) each of the hBNP fragments has an amino acid sequence that preferably includes a portion or all of the amino acids 10 to 26 of hBNP; and (b) each of the human BNP fragments of the composition desirably are cross-linked to at least one of the other human BNP fragments of the composition. The immunoassay preferably comprises the steps of:

(a) immobilizing a hBNP peptide, hBNP fragment, or hBNP analogue thereof onto a solid phase to produce an immobilized hBNP peptide, hBNP fragment, or hBNP analogue thereof;

(b) contacting the immobilized hBNP peptide, hBNP fragment, or hBNP analogue thereof with a test sample suspected of containing the hBNP composition; and (c) contacting the immobilized hBNP peptide, hBNP fragment, or hBNP analogue thereof and the test sample suspected of containing the hBNP composition with at least one antibody or functionally active fragment thereof that has been conjugated to a detectable label to form an immobilized hBNP-antibody complex and a non-immobilized hBNP-antibody complex.

Optionally the immunoassay comprises the further steps:

(d) removing the non-immobilized hBNP-antibody complex, if desired;

(e) optionally determining the amount of immobilized hBNP-antibody complex formed in step (c); and (f) further optionally relating the amount of the immobilized hBNP-antibody complex formed to the amount of the hBNP composition, e.g., via use of a standard curve for hBNP or hBNP fragment.

The detectable label used in the above-described immunoassay preferably can be a radioactive label, an enzymatic label, a chemiluminescent label, a fluorescence label, a thermometric label, an immuno-polymerase chain reaction label, or any other appropriate label.

BRIEF DESCRIPTION OF THE FIGURES

These and other features of the invention will become more apparent in the following detailed description in which reference is made to the appended figures.

FIG. 1 shows that amino acid sequence of human pro-BNP (also known as $BNP_{1-108}$; SEQ ID NO:1) which is a 108-amino acid precursor of human BNP 1-32.

DETAILED DESCRIPTION OF THE INVENTION

I. Definitions

Figure 2:
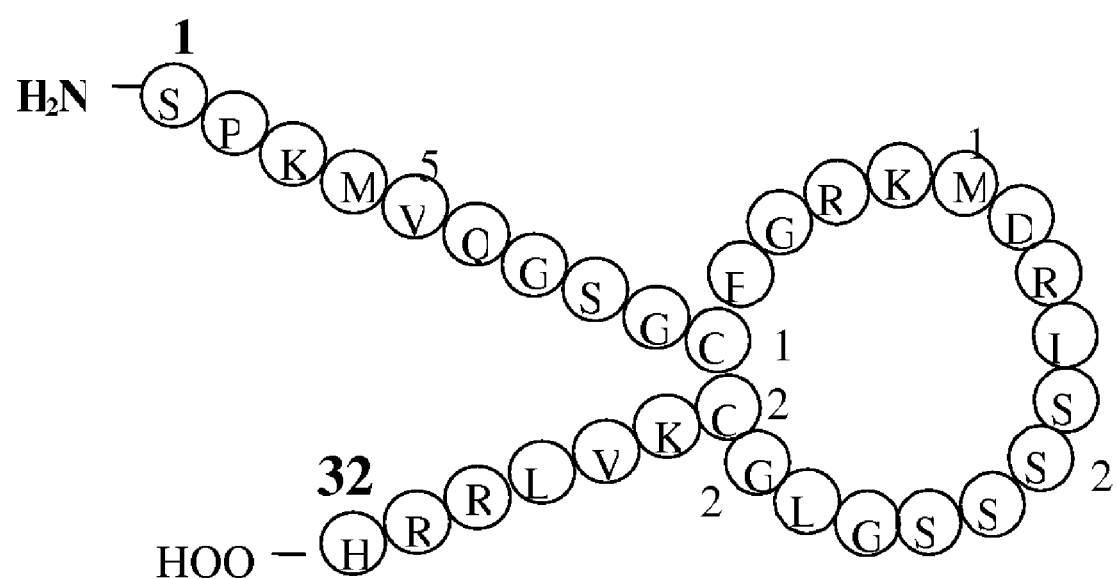
FIG. 2 shows the amino acid sequence of mature human BNP 1-32 (also known as $BNP_{77-108}$; SEQ ID NO:2).

As used herein, the term "antibody" refers to an immunoglobulin molecule or immunologically active portion thereof, namely, an antigen-binding portion. Examples of immunologically active portions of immunoglobulin molecules include F(ab) and F(ab')$_2$ fragments which can be generated by treating an antibody with an enzyme, such as pepsin.

The terms "corresponding to" or "corresponds to" as used herein in relation to an amino acid sequence indicates that the amino acid sequence is substantially identical to a reference amino acid sequence. By "substantially identical" it is meant that, when optimally aligned, for example using the methods described below, the amino acid sequence shares at least 70%, 75%, 80%, 85%, 90%, 95%, 96%, 97%, 98%, 99%, or 100% sequence identity with the reference amino acid sequence. Percent identity between two amino acid sequences is determined in various ways that are within the skill in the art, for instance, using publicly available computer software such as Smith Waterman Alignment (Smith, T. F. and M. S. Waterman, *J Mol Biol,* 147:195-7 (1981)); "BestFit" (Smith and Waterman, *Advances in Applied Mathematics,* 482-489 (1981)); BLAST program (Basic Local Alignment Search Tool; (Altschul, S. F., W. Gish, et al., *J. Mol. Biol.* 215: 403-10 (1990)) and variations and updates thereof; ALIGN, ALIGN-2, CLUSTAL, or Megalign (DNASTAR) software. In addition, those skilled in the art can determine appropriate parameters for measuring alignment, including algorithms needed to achieve maximal alignment over the length of the sequences being compared. In general, for peptides, the length of comparison sequences will be at least 5 amino acids, and preferably at least 10 amino acids, but one skilled in the art will understand that the actual length will depend on the overall length of the sequences being compared and may be at least 12, 15, 17, 18, 19 or 20 amino acids, or it may be the full-length of the peptide sequence.

As used herein, the terms "cross-linked" or "cross-linking", which are used interchangeably herein, when used in connection with a peptide or peptide fragment, refers to the attachment of a peptide or peptide fragment, such as a first hBNP fragment, to a second or another peptide or peptide fragment, such as a second hBNP fragment, by an element, a group or a compound that joins carbon atoms of the one peptide fragment to the second peptide fragment by a chemical bond. The term "cross-linked" or "cross-linking" as used herein can refer to cross-linking which occurs naturally in peptides and peptide fragments. For example, such natural cross-linking includes the cross-linking that occurs when peptides and peptide fragments are joined by disulfide bonds at cysteine residues. Alternatively, cross-linking can be effected artificially, such as by adding chemical substances, such as a cross-linking agent. The location of the cross-linking on the peptide or peptide fragment is not critical. Specifically, the cross-linking between one or more peptides or peptide fragments can occur at any location on an amino acid chain. For example, the cross-linking can occur at either the amino terminus, at carboxy terminus or at both the amino and the carboxy terminus. Alternatively, the cross-linking could occur at any amino acid between the amino terminus and the carboxy terminus.

As used herein, the term "discrete environment" refers to a single medium, such as a single solution, a single gel, a single precipitate, etc.

As used herein, the terms "human brain natriuretic peptide", "human BNP", "hBNP", "hBNP peptide" or "hBNP polypeptide" which are used interchangeably herein, all refer to a 32 amino acid molecule representing amino acids 77-108 of the 108 amino acid precursor molecule of human brain natriuretic peptide (See, FIG. 2). Human brain natriuretic peptide is also referred to herein as the "parent peptide".

The term "hBNP analogue" as used herein includes molecules that mimic the chemical structure of hBNP and retain the functional properties of the hBNP peptide. Examples of hBNP analogues include peptides comprising one or more non-natural amino acids, wherein "non-natural amino acids" (or, "non-naturally occurring amino acids") preferably are those that do not occur in hBNP as found in nature, which include but are not limited to unnatural amino acids (e.g., those having D-stereospecificity), or one or more amino acid that is modified, changed, substituted, or altered when compared the corresponding amino acid in the human BNP peptide (1-32). An hBNP analogue is considered to retain the functional properties of the hBNP peptide when it exhibits acceptable functionality according to the invention, i.e., preferably an ability to compete with or substitute for hBNP, hBNP fragments, Human BNP Fragment Compositions, or combinations thereof in the test sample for binding to the antibody (as conferred by an ability to bind the antibody).

The terms "hBNP fragment" or "hBNP peptide fragment" as used herein refer to a polypeptide that comprises at least three contiguous amino acids of amino acids 77-108 (1-32) of the 108 amino acid BNP precursor molecule of human brain natriuretic peptide, but comprises less amino acids than the complete parent peptide.

In one embodiment, a hBNP fragment or hBNP peptide fragment refers to a polypeptide that preferably comprises at least five contiguous amino acids residues of amino acids 77-108 (1-32) of the 108 amino acid BNP precursor molecule, but less amino acids than the complete parent peptide; even more preferably that comprises at least ten contiguous amino acids residues of amino acids 77-108 (1-32) of the 108 amino acid BNP precursor molecule, but less amino acids than the complete parent peptide; optionally that comprises at least fifteen (15) contiguous amino acids residues of amino acids 77-108 (1-32) of the 108 amino acid BNP precursor molecule, but less amino acids than the complete parent peptide; desirably that comprises at least twenty (20) contiguous amino acids residues of amino acids 77-108 (1-32) of the 108 amino acid BNP precursor molecule, but less than amino acids the complete parent peptide; even more desirably that comprises at least twenty-five (25) contiguous amino acid residues of amino acids 77-108 (1-32) of the 108 amino acid BNP precursor molecule, but less amino acids than the complete parent peptide.

In another embodiment, a hBNP fragment or hBNP peptide fragment refers to a polypeptide that preferably comprises contiguous amino acid residues having one of the following formulas: (1) a-32, wherein a is an integer selected from the group consisting of, 2, 3, 4, 5, 6, 7, 8, 9, 10, 11, 12, 13, 14, 15, 16, 17, 18, 19, 20, 21, 22, 23, 24, 25, 26, 27, 28, 29 and 30; (2) b -31, wherein b is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28 and 29; or (3) c-30, wherein c is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27 and 28.

In another embodiment, a hBNP fragment or hBNP peptide fragment refers to a polypeptide that preferably includes a portion of or all of amino acid residues 10 to 26 of human BNP. For example, hBNP fragments or hBNP fragments according to the invention that have an amino acid sequence that includes a portion of or all of amino acids 10 to 26 of human BNP include those selected from the group consisting of polypeptides comprising consecutive amino acids residues 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 3-14, 3-13, 3-12, 3-11, 3-10, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 6-14, 6-13, 6-12, 6-11, 6-10, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 7-14, 7-13, 7-12, 7-11, 7-10, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 8-12, 8-11, 8-10, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 9-14, 9-13, 9-12, 9-11, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 10-14, 10-13, 10-12, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 11-14, 11-13, 12-32, 12-31, 12-30, 12-29, 12-28, 12-27, 12-26, 12-25, 12-24, 12-23, 12-22, 12-21, 12-20, 12-19, 12-18, 12-17, 12-16, 12-15, 12-14, 13-32, 13-31, 13-30, 13-29, 13-28, 13-27, 13-26, 13-25, 13-24, 13-23, 13-22, 13-21, 13-20, 13-19, 13-18, 13-17, 13-16, 13-15, 14-32, 14-31, 14-30, 14-29, 14-28, 14-27, 14-26, 14-25, 14-24, 14-23, 14-22, 14-21, 14-20, 14-19, 14-18, 14-17, 14-16, 15-32, 15-31, 15-30, 15-29, 15-28, 15-27, 15-26, 15-25, 15-24, 15-23, 15-22, 15-21, 15-20, 15-19, 15-18, 15-17, 16-32, 16-31, 16-30, 16-29, 16-28, 16-27, 16-26, 16-25, 16-24, 16-23, 16-22, 16-21, 16-20, 16-19, 16-18, 17-32, 17-31, 17-30, 17-29, 17-28, 17-27, 17-26, 17-25, 17-24, 17-23, 17-22, 17-21, 17-20, 17-19, 18-32, 18-31, 18-30, 18-29, 18-28, 18-27, 18-26, 18-25, 18-24, 18-23, 18-22, 18-21, 18-20, 19-32, 19-31, 19-30, 19-29, 19-28, 19-27, 19-26, 19-25, 19-24, 19-23, 19-22, 19-21, 20-32, 20-31, 20-30, 20-29, 20-28, 20-27, 20-26, 20-25, 20-24, 20-23, 20-22, 21-32, 21-31, 21-30, 21-29, 21-28, 21-27, 21-26, 21-25, 21-24, 21-23, 22-32, 22-31, 22-30, 22-29, 22-28, 22-27, 22-26, 22-25, 22-24, 23-32, 23-31, 23-30, 23-29, 23-28, 23-27, 23-26, 23-25, 24-32, 24-31, 24-30, 24-29, 24-28, 24-27, 24-26, 25-32, 25-31, 25-30, 26-29 and 26-28 of human BNP.

As used herein, the term "immunogenic carrier(s)" refers to proteins, glycoproteins, complex polyamino-polysaccharides, particles and nucleic acids that are recognized as foreign and thereby elicit an immunologic response from a host. The polyamino-polysaccharides can be prepared from polysaccharides using any means known in the art for their preparation. Examples of proteins that can be used, include, but are not limited to, albumins, serum proteins, lipoproteins, and other similar compounds (more specifically, bovine serum albumin ("BSA"), keyhole limpet hemocyanin ("KLH"), egg ovalbumin, bovine thyroglobulin ("BTG"), and the like).

As used herein, the term "purified" when used in connection with a peptide, peptide fragment or polypeptide, does not require absolute purity. Rather, the term "purified" represents an indication that a peptide(s), peptide fragment(s) or polypeptide of interest is (are) in a discrete environment in which abundance (based on mass) relative to other proteins is greater than in a test sample. Purified peptides, peptide fragments or polypeptides may be obtained by any techniques known by those skilled in the art, including, but not limited to, laboratory synthesis, chromatography, preparative electrophoresis, centrifugation, precipitation, affinity purification, etc. One or more "purified" peptides, peptide fragments or polypeptides of interest are preferably at least 10% of the protein content of the discrete environment. One or more "substantially purified" peptides, peptide fragments or polypeptides are at least 50% of the protein content of the discrete environment, more preferably, at least 75% of the protein content of the discrete environment, and most preferably at least 95% of the protein content of the discrete environment. Protein content can be determined using a modification of the method of Lowry et al., *J. Biol. Chem.*, 193:265 (1951), described by Hartree, *Anal. Biochem.*, 48:422-227 (1972), using bovine serum albumin as a protein standard.

As used herein, the terms "subject" and "patient" are used interchangeably. As used herein, the terms "subject" and "subjects" refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomolgous monkey, chimpanzee, and a human).

As used herein, the term "test sample" refers to a biological sample derived from serum, plasma, whole blood, lymph, CNS fluid, urine or other bodily fluids of a subject. Preferably such samples are isolated and testing is done in vitro. The test samples can be from any source, but preferably are human. The test sample can be prepared (e.g., isolated, and optionally, pretreated prior to use in testing) using routine techniques known to those skilled in the art.

According to the present invention, peptides and amino acids can be naturally occurring, non-naturally occurring, modified, or synthetic. Amino acids are identified herein by their conventional three-letter or one-letter abbreviations, which are generally accepted in the peptide art and, e.g., recommended by the IUPAC-IUB commission in biochemical nomenclature.

II. Human BNP Fragment Compositions of the Present Invention

In one embodiment, the present invention relates to a peptide composition. In one aspect, the composition of the present invention preferably comprises at least two (2) human BNP fragments. Each of the human BNP fragments that comprise the composition preferably are cross-linked to at least one of the other human BNP fragments that constitute or comprise the composition. The cross-linking between the human BNP fragments of the composition may occur naturally, artificially, or by a combination of natural and artificial methods. For example, if the composition comprises two (2) human BNP fragments, the fragments optionally may be cross-linked naturally to each another via one or more disulfide bonds at cysteine residues contained in each of the human BNP fragments. In addition, the at least two (2) human BNP fragments preferably are purified (such as, but not limited to, for use as an immunogen). For convenience purposes, the compositions described herein are collectively referred to as "Human BNP Fragment Composition(s)".

As mentioned briefly above, the cross-linking between human BNP fragments of the Human BNP Fragment Composition may occur naturally. Such a Human BNP Fragment Composition preferably may be obtained by treating a test sample known to contain or containing human BNP or a human BNP fragment with at least one chemical or compound that is known to cleave at least one amino acid residue of human BNP or a human BNP fragment. An example of a compound that is that is known to cleave at least one amino acid residue of human BNP or a human BNP fragment is an enzyme. It is preferred that the enzyme used to prepare the Human BNP Fragment Composition be capable of cleaving at least one amino acid residue that is known to constitute the "ring" of human BNP. The "ring" of human BNP comprises amino acids 10-26 of human BNP. Examples of enzymes which are known to cleave human BNP and human BNP fragments, include, but are not limited to, trypsin, Arg-C endoprotease, Asp-N endoprotease and Lys-C endoprotease. It is known in the art that trypsin cleaves lysine (K) residues in human BNP and human BNP fragments. It is known in the art that Arg-C endoproteases cleave arginine (R) residues in human BNP and human BNP fragments. It is known in the art that Asp-N endoproteases cleave asparagine (D) residues in human BNP and human BNP fragments. It is known in the art that Lys-C endoproteases cleave methionine (M) residues in human BNP and human BNP fragments. Alternatively, such a Human BNP Fragment Composition may be obtained by treating a test sample known to contain human BNP or a human BNP fragment with a compound or chemical that is known to degrade human BNP or human BNP fragments. Preferably, such a compound or chemical is known to degrade human BNP or human BNP fragments at specific amino acid residues, more preferably, at one specific amino acid residue. For example, an example of a compound that is known to degrade human BNP or human BNP fragments at specific residues is cyanogen bromide. More specifically, cyanogen bromide is known in the art to cleave methionine residues selectively under acidic conditions. The reaction conditions, such as, but not limited to, time, temperature and pH, for performing such degradation of human BNP or human BNP fragments are routine and are well-known to those skilled in the art.

Alternatively, the human BNP fragments comprising the Human BNP Fragment Compositions may be cross-linked artificially. Specifically, the human BNP fragments comprising the Human BNP Fragment Compositions preferably are cross-linked using routine cross-linking techniques known to those skilled in the art. For example, such cross-linking can be effected via the use of at least one cross-linking agent (a variety of cross-linking agents are available commercially, such as, but not limited to, those from Pierce Chemical Company (Pierce and Warriner, Chester, U.K.)), or at least one cross-linker or coupling agent (a variety of cross-linkers are available commercially, such as, but not limited to, those from Pierce Chemical Company (Pierce and Warriner, Chester, U.K.). An example of a cross-linker that can be used includes, but is not limited to, 1-ethyl-3-[3-dimethylaminopropyl]carbodiimide hydrochloride ("EDC" or "EDAC")), or a combination of at least one cross-linking agent and at least one cross-linker (See, e.g., Greg T. Hermanson, *Bioconjugate Techniques*, Academic Press, (1996)). More specifically, preferably at least two human BNP fragments are designed and synthesized chemically to contain one or more reactive functional groups (namely, side chains) on one or more amino acid residues of each of the human BNP fragments, using routine techniques known in the art. Examples of reactive functional groups that can be used, include, but are not limited to, a —SH group, a —NH$_2$ group, a —N$_3$ group, a —COOH group, a —CHO group, a —Br group, a —C≡CH group, an —ONH$_2$ group, etc. Alternatively, preferably no cross-linking agent or cross-linker may be required to effectuate cross-linking between two or more human BNP fragments comprising the Human BNP Fragment Compositions.

Specifically, one or more amino acids carrying one or more reactive functional groups on a side chain preferably can be introduced into one or more human BNP fragments using solid phase peptide synthesis, which is a routine technique known to those skilled in the art. The appropriate reactive functional group can then be chemoselectively reacted to cross-link the human BNP fragments to obtain the desired selectively cross-linked human BNP fragments (and thus the Human BNP Fragment Composition). Alternatively, a cross-linker can also preferably be used to cross-link at least two human BNP fragments. As mentioned previously herein, EDAC is an example of a cross-linker that can be used. EDAC can be used to couple one or more human BNP fragments that contain a free —COOH with one or more second human BNP Fragments that contain a free —NH$_2$, thus resulting in selectively cross-linked human BNP Fragments (and thus the Human BNP Fragment Composition). Examples of other cross-linking or coupling reagents that can be used to cross-link one or more human BNP fragments to one another include, but are not limited to, benzotriazole-1-yl-oxy-tris-(dimethylamino)-phosphinumhexafluorophosphate ("BOP"), 1,1'-Carbonyl-diimidazole ("CDI"), 1-(1H-Benzotriazole-1-yl)-1,1,3,3-tetramethyluronium hexafluorophosphate ("HBTU"), and the like (See, e.g., Chapter 9—"Convergent Peptide Synthesis" in FMOC Solid Peptide Synthesis: A Practical Approach by W. C. Chan and P. D. White, Oxford University Press (2000)). These cross-linking or coupling reagents preferably can be used to couple one or more human BNP fragments having a free —COOH to one or more human BNP fragments having a free —NH$_2$ in non-aqueous solvents, provided that all of the side-chains in all the human BNP fragments involved in the reaction are protected.

For example, the Human BNP Fragment Compositions preferably can comprise two (2) human BNP fragments which are prepared synthetically using routine techniques known in the art. The first human BNP fragment can be designed and chemically synthesized to contain at least one functional group (namely, a side-chain) on one or more amino acids, such as a CH$_2$NH$_2$ group, and then purified. The second human BNP fragment can be designed and chemically synthesized to contain at least one functional group (namely, a side-chain) on one or more amino acids, such as a CH$_2$COOH group, and then purified. The side-chains of the first and second human BNP fragments can then reacted with a cross-linking agent to form an amide bond and thus cross-link the first human BNP fragment with the second human BNP fragments (and thus forming a Human BNP Fragment Composition).

By way of yet another example, if a Human BNP Fragment Composition comprises three (3) human BNP fragments (namely, a first human BNP fragment, a second human BNP fragment, and a third human BNP fragment (one of which, two of which, or all of which can optionally be labeled with a detectable label using routine techniques known in the art, which are discussed in more detail infra)), then each of the first, second, and third human BNP fragments preferably can be designed and chemically synthesized to contain one or more functional groups (namely, side chains) on one or more amino acids that can be chemically (or chemoselectively) reacted to form a chemical bond, thus cross-linking the human BNP fragments. For example, the first human BNP fragment preferably can be designed and chemically synthesized to contain two functional groups on one or more amino acids, and then purified. A first functional group can be, e.g., a CH$_2$N$_3$ group, and the second functional group can be, e.g., a CHO group. The second human BNP fragment can be designed and chemically synthesized to contain a functional group, such as, e.g., a CH$_2$C≡CH group, and then purified. The third human BNP fragment can be designed, chemically synthesized to contain a functional group, such as, e.g., a CH$_2$ONH$_2$ group, and then purified. The functional groups of the first, second, and third human BNP fragments optimally can then be chemically reacted (e.g., Sreenivas Punna et al., *Angew Chem. Int. Ed. Eng.*, 117:2255-2260 (2005)) to form a triazine bond, and thus a cross-link between the first and second human BNP fragments. Then, either simultaneously, sequentially, or prior to the formation of the cross-link between the first and second human BNP fragments, optionally the functional groups of the first (CHO) and third (CH$_2$ONH$_2$) human BNP fragments can then be chemically reacted (See, Hang et al., *Acc. Chem. Res.*, 34:727 (2001)) to form an oxime bond and thus a cross-link between the first and the third human BNP fragments (and thus forming a Human BNP Fragment Composition). The order in which the cross-linking is performed between the first, second and third human BNP fragments is not critical (and can be appropriately modulated based on selective groups).

As mentioned above, the present invention provides that the at least two (2) human BNP fragments comprising the Human BNP Fragment Composition preferably are prepared synthetically. The present invention further contemplates that one or more of human BNP fragments preferably contain at least one amino acid residue that is modified, changed, substituted, or altered when compared the corresponding amino acid in the human BNP peptide (1-32). Such a modification, change, substitution or alteration can be made to allow for the cross-linking of the at least two (2) human BNP fragments. Methods for modifying, changing, substituting or altering amino acids are well known in the art (See, Greg T. Hermanson, *Bioconjugate Techniques*, Academic Press, (1996)). Preferably, the amino acid changes are of a minor nature, e.g., such that the amino acid sequence of the human BNP fragments comprising the human BNP Fragment Composition preferably corresponds to that of the human BNP peptide (1-32). That is, conservative amino acid substitutions are preferred that preferably do not significantly affect the function or activity of the peptide; small deletions, typically of one to six amino acids; small amino- or carboxyl-terminal extensions; a small linker peptide; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions, which do not generally alter the specific activity are known in the art and are described, for example, by H. Neurath and R. L. Hill, in, *The Proteins*, Academic Press, New York (1979). The most commonly occurring exchanges are Ala/Ser, Val/Ile, Asp/

Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The present invention thus also preferably provides human BNP fragments containing minor amino acid residue variations when compared to the corresponding amino acids in human BNP peptide (1-32).

Alternatively, the human BNP fragments that comprise the Human BNP Fragment Composition preferably may be cross-linked both naturally and artificially. For example, if the BNP Fragment Composition comprises three (3) human BNP fragments (namely, a first human BNP fragment, a second human BNP fragment, and a third human BNP fragment), then the first human BNP fragment preferably may be cross-linked to the second human BNP fragment via disulfide binds at cysteine residues contained within each of the first and second human BNP fragments. The third human BNP fragment preferably may be cross-linked to the second human BNP fragment synthetically using routine techniques known in the art and described herein. For example, the second human BNP fragment optionally can be designed, chemically synthesized and purified to contain a side-chain that contains, e.g., a sulfide group (—SH). The third human BNP fragment can be designed and synthesized to contain a side-chain that contains, e.g., $CH_2Br$. Preferably the side-chains of the second and third human BNP fragments are then chemically reacted to form a thio ether bond (a linker) and thus a cross-link between the second and third human BNP fragments.

Figure 5:
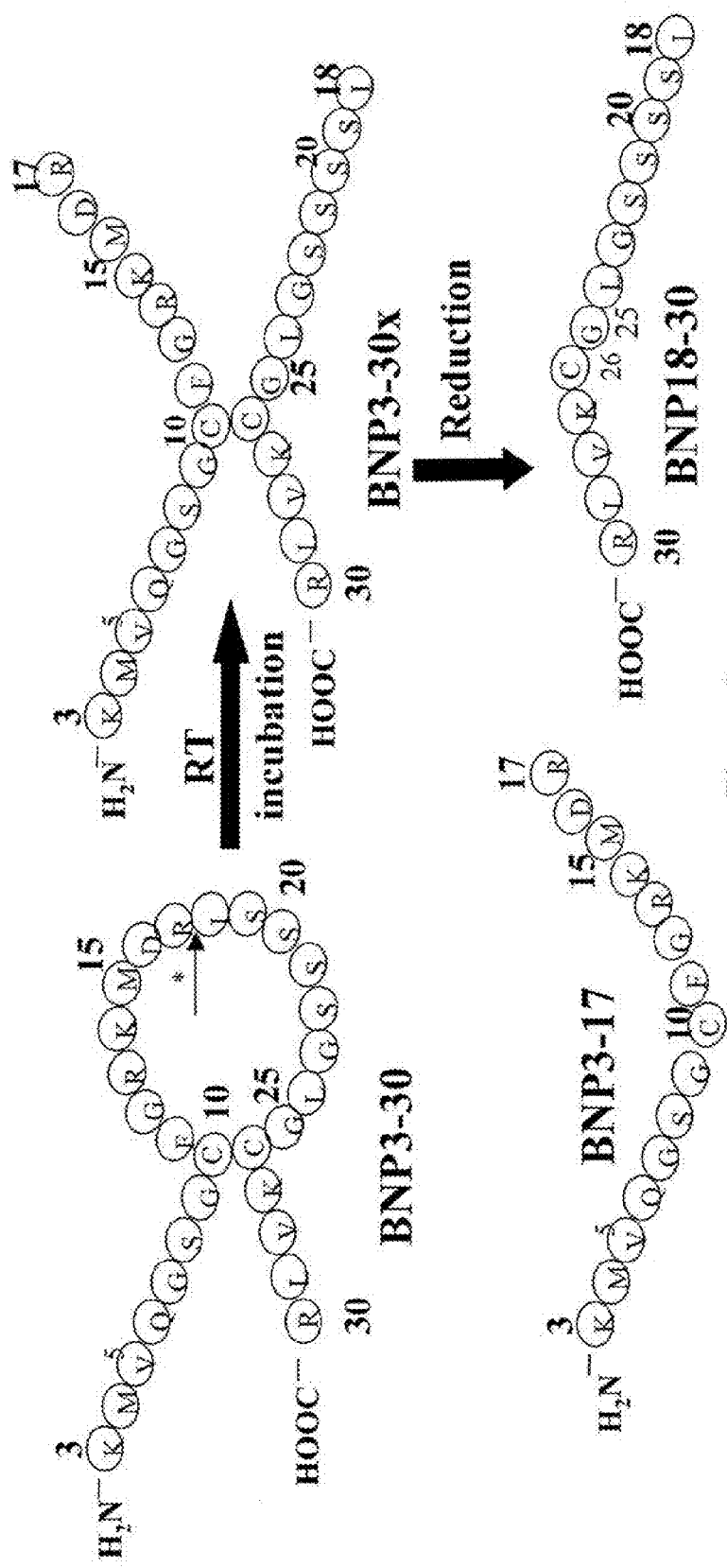
FIG. 5 provides an illustration of human BNP ring cleavage and cleavage site identification: Main degradation product human BNP fragment 3-30 ("BNP3-30") (SEQ ID NO: 4) undergoes further degradation to the Human BNP Fragment Composition 3-30x ("BNP3-30x") (including SEQ ID NOs: 5 and 6), with ring cleavage. Identification of the further reduction products of the ring-cleavage products ("BNP18-30" (SEQ ID NO: 6) and "BNP3-17" (SEQ ID NO: 5)) pinpoints the cleavage site(s) (i.e., indicated by the asterisk and arrow in BNP3-30, and the disulfide bond between Cys-10 and Cys-25 in BNP3-30x).
Figure 11:
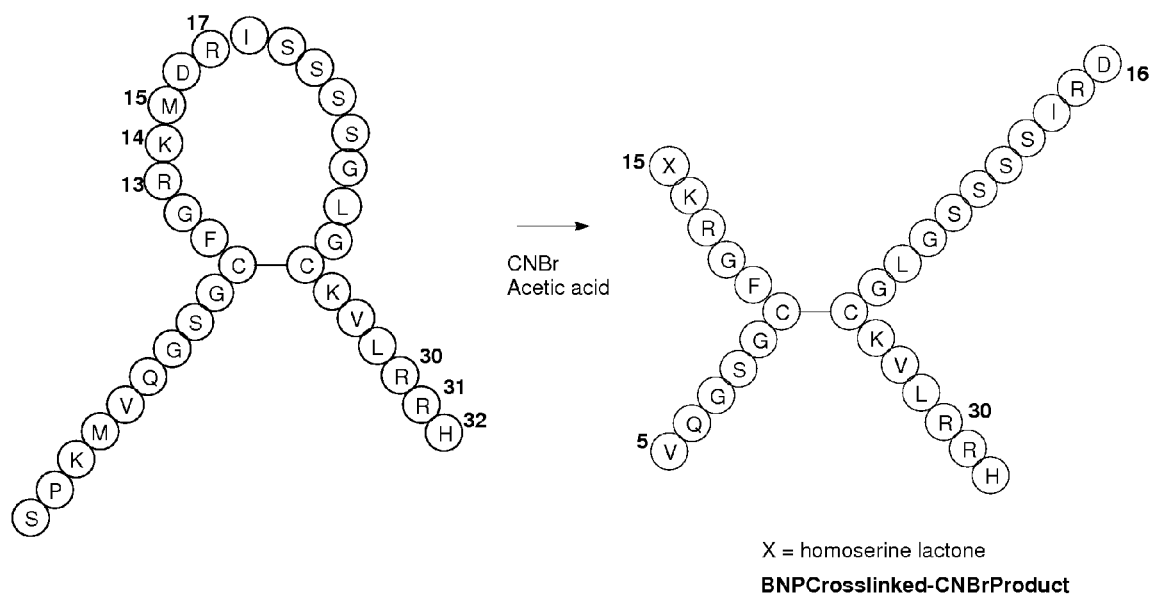
FIG. 11 shows a BNP Fragment Composition (defined herein) generated via chemical degradation using cyanogen bromide cleavage. On the left side of the reaction is BNP1-32 (SEQ ID NO: 2). On the right side of the reaction are BNP5-15 (SEQ ID NO: 7) and BNP16-32 (SEQ ID NO: 8) fragments that are cross-linked.
Figure 13:
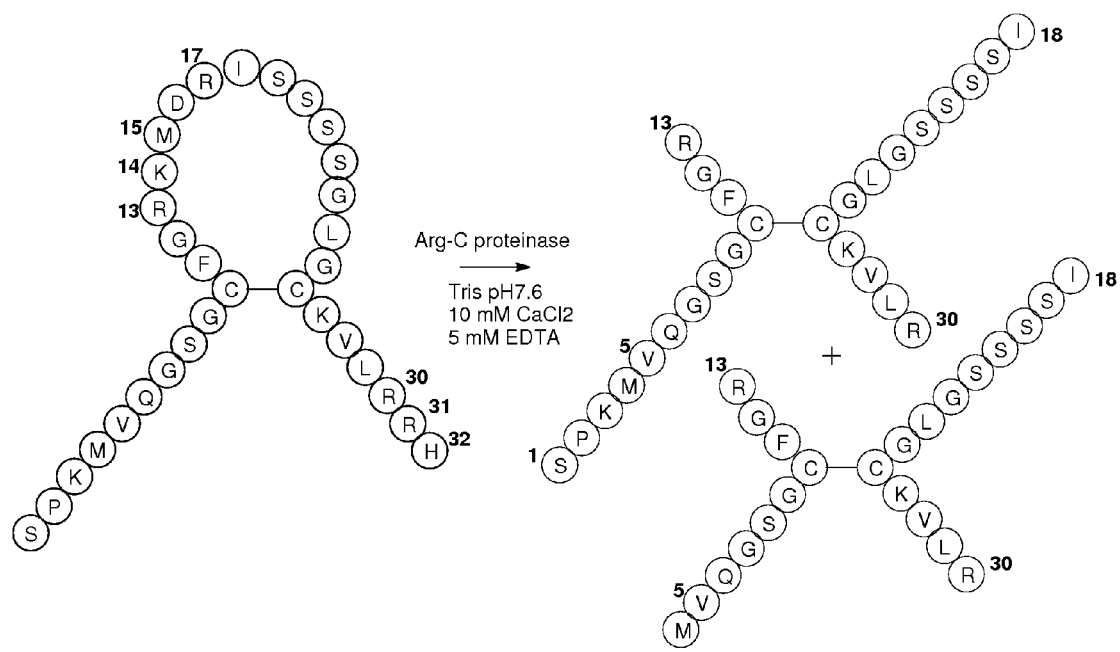
FIG. 13 shows the enzymatic generation of Arginase-C (Arg-C) of a Human BNP Fragment Composition (as defined herein). On the left side of the reaction is BNP1-32 (SEQ ID NO: 2). On the right side of the reaction are BNP1-13 (SEQ ID NO: 9) and BNP18-30 (SEQ ID NO: 6) that cross-linked, and BNP4-13 (SEQ ID NO: 10) and BNP18-30 (SEQ ID NO: 6) that are cross-linked.

As mentioned previously, some of the Human BNP Fragment Compositions according to the invention preferably exhibit an "X" like shape as depicted in FIGS. 5, 11, and 13. However, other shapes are possible, e.g., an X-like shape with one or more arms truncated, so as to form, for instance, a Y— or inverted Y-shaped structure.

III. Immunogens and Antibodies

In another aspect, the present invention relates to immunogens. More specifically, the immunogens of the present invention preferably comprise at least one of the Human BNP Fragment Compositions described previously herein. The Human BNP Fragment Composition described herein optionally can be conjugated to one or more immunogenic carriers using routine techniques known to those skilled in the art and used as an immunogen. Additionally one or more carriers and/or diluents preferably can be employed with the immunogen as well. Carriers and diluents include, but are not limited to, sterile liquids, such as water and oils, with or without the addition of a surfactant and other pharmaceutically and physiologically acceptable carrier, including adjuvants, excipients or stabilizers. Examples of oils that can be used include but are not limited to those of petroleum, animal, vegetable or synthetic origin, such as peanut oil, soybean oil or mineral oil. In general, water, saline, aqueous dextrose and related sugar solution and glycols, such as propylene glycol or polyethyelene glycol, optionally can be used as liquid carriers, particularly for injectable solutions.

In another aspect, the present invention preferably relates to an antibody that is produced using the immunogens of the present invention. The antibody optionally can be a polyclonal, monoclonal, recombinant (such as, but not limited to, a chimeric or humanized), fully human or non-human (such as, but not limited to, a murine antibody) or a single chain antibody. Moreover, the antibody optionally can be coupled to a detectable label. Detectable labels and their attachment to antibodies are discussed in more detail infra.

Methods for making polyclonal antibodies are well known to those skilled in the art. More specifically, the immunogen (which as discussed previously herein, can be conjugated to one or more immunogenic carriers), can be administered to an animal using routine techniques known in the art, the blood then collected and the serum or IgG fraction containing the antibodies then obtained.

Methods for making monoclonal antibodies are also well known to those skilled in the art. Any technique which provides antibodies produced by continuous cell line cultures can be used. Examples include the hybridoma technique (Kohler, G. and Milstein, C., *Nature,* 256:495-497 (1975)), the trioma technique, and the human B-cell hybridoma technique (Cole et al., *Monoclonal Antibodies and Cancer Therapy*, pp. 77-96, Alan R. Liss, Inc., (1985)).

Methods for making recombinant antibodies are also well known to those skilled in the art and are described, for example, in Morrison et al., *Proc. Natl. Acad. Sci.,* U.S.A., 81:8651-6855 (1984), Neuberger et al., *Nature,* 312:604-608 (1984), Takeda et al., *Nature,* 314:452-454 (1985). For example, chimeric antibodies can be made by splicing the genes from a mouse antibody molecule specific for epitopes of a Human BNP Fragment Composition with genes from a human antibody molecule of appropriate biological activity.

Completely human antibodies can be produced using transgenic mice that are incapable of expressing endogenous immunoglobulin heavy and light chain genes, but which can express human heavy and light chain genes (See, for example, Lonberg and Huszar, *Int. Rev. Immunol.,* 13:65-93 (1995) and U.S. Pat. Nos. 5,625,126, 5,633,425, 5,569,825, 5,661,016, and 5,545,806). Companies such as Abgenix, Inc. (Fremont, Calif.) and Medarex, Inc. (Princeton, N.J.) can be engaged to provide human antibodies directed against selected antigens using technology similar to that described above.

Additionally, completely human antibodies that recognize a selected epitope can be generated using a technique known as "guided selection". In this approach, a selected non-human monoclonal antibody (such as, but not limited to, a murine antibody), is used to guide the selection of a completely human antibody recognizing the same epitope (See, Jespers et al., *Bio/Technology,* 12:899-903 (1994)).

The antibody of the present invention also preferably can be a single-chain antibody (hereinafter "scFV"). A scFV can be made as described in Colcher, D., et al., *Ann. NY Acad. Sci.,* 30:880:263-280 (June 1999) and Reiter, Y., *Clin. Cancer Res.,* 2(2):245-252 (February 1996). The single chain antibody can be dimerized or multimerized to generate multivalent antibodies having specificities for different epitopes of the same target as the Human BNP Fragment Compositions described herein.

The antibodies described herein can be used for a number of purposes. For example, the antibodies can be used to isolate human BNP, human BNP fragments, Human BNP Fragment Compositions, or combinations thereof using standard techniques, such as affinity chromatography or immunoprecipitation. Moreover, preferably the antibodies of the present invention can be used in immunoassays to determine the amount of human BNP, human BNP fragments, Human BNP Fragment Compositions or combinations thereof in immunoassays as discussed in more detail infra.

IV. Immunoassays

In another aspect, the present invention relates to immunoassays that preferably can be used for the qualitative and/or quantification of the hBNP, hBNP fragments, Human BNP Fragment Compositions, or combinations thereof in a test sample. The immunoassays of the present invention preferably can be conducted using any format known in the art, such as, but not limited to, a sandwich format, a competitive inhibition format (including both forward or reverse competitive inhibition assays), or in a fluorescence polarization format.

In immunoassays for the qualitative detection of hBNP, hBNP fragments, Human BNP Fragment Compositions, or combinations thereof in a test sample, preferably at least one antibody that binds to certain epitopes of hBNP, hBNP fragments, Human BNP Fragment Compositions or combinations thereof is contacted with at least one test sample suspected of containing or that is known to contain hBNP, hBNP fragments, Human BNP Fragment Compositions or combinations thereof to form an antibody-hBNP immune complex. The antibodies described in Section II herein, for example, can be used in such immunoassays to form such antibody-hBNP immune complexes in at least one test sample. These immune complexes preferably can then be detected using routine techniques known to those skilled in the art. For example, the antibody of the present invention preferably can be labeled with a detectable label to detect the presence antibody-hBNP complex. Alternatively, the hBNP, hBNP fragments, Human BNP Fragment Compositions, or combinations thereof in the test sample optionally can be labeled with a detectable label and the resulting antibody-hBNP immune complexes detected using routine techniques known to those skilled in the art. Detectable labels and their attachment to antibodies are discussed in more detail infra.

Alternatively, a second antibody that binds to the hBNP, hBNP fragments, Human BNP Fragment Compositions, or combinations thereof and that contains a detectable label preferably can be added to the test sample and used to detect the presence of the antibody-hBNP complex. Any detectable label known in the art can be used. Detectable labels and their attachment to antibodies are discussed in more detail infra.

In immunoassays for the quantitative detection of BNP, such as a sandwich type format, optionally at least two antibodies are employed to separate and quantify hBNP, hBNP fragments, Human BNP Fragment Compositions, or combinations thereof in a test sample. More specifically, preferably the at least two antibodies bind to certain epitopes of hBNP, hBNP fragments, Human BNP Fragment Compositions, or combinations thereof forming an immune complex which is referred to as a "sandwich". Generally, one or more antibodies can be used to capture the hBNP, hBNP fragments, Human BNP Fragment Compositions, or combinations thereof in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies).

In a sandwich assay according to the invention, it is preferred that both antibodies' binding to their epitopes are not diminished by the binding of any other antibody in the assay to its respective epitope. In other words, antibodies preferably should be selected so that the one or more first antibodies brought into contact with a test sample suspected of containing hBNP, hBNP fragments, Human BNP Fragment Compositions, or combinations thereof do not bind to all or part of an epitope recognized by the second or subsequent antibodies, thereby interfering with the ability of the one or more second detection antibodies to bind to the hBNP, hBNP fragments, Human BNP Fragment Compositions, or combinations thereof.

A sandwich immunoassay preferably can be performed using the antibodies described previously herein. More specifically, the antibodies of the present invention desirably can be used as a first antibody in the immunoassay. Preferably, the antibody of the present invention immunospecifically binds to epitopes comprising at least three (3) amino acids of hBNP, hBNP fragments, Human BNP Fragment Compositions, or combinations thereof. In addition to the antibodies of the present invention, the immunoassay optionally comprises a second antibody, preferably a monoclonal antibody, that immunospecifically binds to epitopes having an amino acid sequence comprising at least three (3) amino acids of amino acids hBNP, hBNP fragments, Human BNP Fragment Compositions, or combinations thereof. For example, a monoclonal antibody produced by hybridoma cell line BC203, which immunospecifically binds to epitopes having an amino acid sequence containing amino acids 27-32 of hBNP, can be used.

In a preferred embodiment, the test sample suspected of containing hBNP, hBNP fragments, Human BNP Fragment Compositions, or combinations thereof preferably can be contacted with at least one first capture antibody (or antibodies) and at least one second detection antibodies, optionally, either simultaneously or sequentially. In the sandwich assay format, preferably a test sample suspected of containing hBNP, hBNP fragments, Human BNP Fragment Compositions, or combinations thereof is first brought into contact with the at least one first capture antibody that specifically binds to a particular epitope under conditions which allow the formation of a first antibody-hBNP complex. If more than one capture antibody is used, desirably a first multiple capture antibody-hBNP complex is formed. In a sandwich assay, the antibodies, preferably, the at least one capture antibody, are used in molar excess amounts of the maximum amount of hBNP, hBNP fragments, Human BNP Fragment Compositions, or combinations thereof expected in the test sample. For example, optionally, from about 5 μg/mL to about 1 mg/mL of antibody per mL of microparticle coating buffer can be used.

Optionally, prior to contacting the test sample with the at least one first capture antibody, the at least one first capture antibody can be bound to a solid support which desirably facilitates the separation of the first antibody-hBNP complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent, or by other means known in the art, provided that such binding does not interfere with the ability of the antibody to bind hBNP, hBNP fragments, Human BNP Fragment Compositions, or combinations thereof. Moreover, if necessary or desired, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing hBNP, hBNP fragments, Human BNP Fragment Compositions, or combinations thereof is brought into contact with the at least one first capture antibody, preferably the test sample is incubated in order to allow for the formation of a first capture antibody (or multiple antibody)-hBNP complex. The incubation can be carried out at a pH of from about 4.5 to about 10.0, preferably at a temperature of from about 2° C. to about 45° C., and desirably for a period from at least about one (1) minute to about eighteen (18) hours, preferably from about 2 to about 6 minutes, most preferably from about 3 to about 4 minutes.

After formation of the first/multiple capture antibody-hBNP complex, preferably the complex is then contacted with at least one second detection antibody (optimally under conditions which allow for the formation of a first/multiple antibody—hBNP-second antibody complex). If the first antibody-hBNP complex is contacted with more than one detection antibody, then preferably a first/multiple capture antibody-hBNP-multiple antibody detection complex is formed. As with first antibody, when the at least one second (and subsequent) antibody is brought into contact with the first antibody-hBNP complex, preferably a period of incubation under conditions similar to those described above is provided for the formation of the first/multiple antibody-hBNP-second/multiple antibody complex. Preferably, the at least one second antibody contains a detectable label. The detectable label optionally can be bound to the at least one second antibody prior to, simultaneously with or after the formation of the first/multiple antibody-hBNP-second/multiple antibody complex. Any detectable label known in the art can be used. For example, the detectable label c an be a radioactive label (such as, e.g., $^3$H, $^{25}$I, $^{35}$S, $^{14}$C, $^{32}$P, and $^{33}$P), an enzymatic label (such as, e.g., horseradish peroxidase, alkaline peroxidase, glucose 6-phosphate dehydrogenase, and the like), a chemiluminescent label (such as, e.g., acridinium esters, luminal, isoluminol, thioesters, sulfonamides, phenanthridinium esters, and the like), a fluorescence label (such as, e.g., fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label optionally can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, e.g., N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The first antibody/multiple-hBNP-second/multiple antibody complex can be, but optionally does not have to be, separated from the remainder of the test sample prior to quantification of the label. For example, if the at least first capture antibody is bound to a solid support, such as a well or a bead, separation preferably can be accomplished by removing the fluid (from the test sample) from contact with the solid support. Alternatively, if the at least first capture antibody is bound to a solid support it preferably can be simultaneously contacted with the hBNP-containing sample and the at least one second detection antibody to form a first (multiple) antibody-hBNP-second (multiple) antibody complex, followed by removal of the fluid (test sample) from contact with the solid support. If at least first capture antibody is not bound to a solid support, then the first antibody/multiple-hBNP-second/multiple antibody complex optionally does not have to be removed from the test sample for quantification of the amount of the label.

After formation of the labeled first antibody-hBNP-second antibody complex, the amount of label in the complex optionally is quantified using techniques known in the art. For example, if an enzymatic label is used, the labeled complex preferably is reacted with a substrate for the label that gives a quantifiable reaction such as the development of color. If the label is a radioactive label, the label preferably is quantified using a scintillation counter. If the label is a fluorescent label, the label preferably is quantified by stimulating the label with a light of one color (which is known as the "excitation wavelength") and detecting another color (which is known as the "emission wavelength") that is emitted by the label in response to the stimulation. If the label is a chemiluminescent label, the label preferably is quantified detecting the light emitted either visually or by using luminometers, x-ray film, high speed photographic film, a CCD camera, and the like. Once the amount of the label in the complex has been quantified, preferably the concentration of hBNP, hBNP fragments, Human BNP Fragment Compositions, or combinations thereof in the test sample is determined, e.g., by use of a standard curve that has been generated using serial dilutions of hBNP, hBNP fragments, Human BNP Fragment Compositions, or combinations thereof of known concentration. Other than using serial dilutions of hBNP, hBNP fragments, Human BNP Fragment Compositions, or combinations thereof, the standard curve can be generated gravimetrically, by mass spectroscopy, and by other techniques known in the art.

In a forward competitive format, preferably an aliquot of labeled hBNP, hBNP fragments, Human BNP Fragment Compositions or combinations thereof thereof of a known concentration is used to compete with hBNP, hBNP fragments, Human BNP Fragment Compositions, or combinations thereof in a test sample for binding to hBNP antibody (such as an antibody of the present invention). Peptides of hBNP and hBNP fragments and methods of making peptides of hBNP and hBNP fragments are known in the art (See, for example, U.S. Pat. No. 6,162,902). Human BNP Fragment Compositions and methods for making Human BNP Fragment Compositions are described supra herein.

In a forward competition assay, an immobilized antibody (such as an antibody of the present invention) optionally can either be sequentially or simultaneously contacted with the test sample and a labeled hBNP, hBNP fragments, Human BNP Fragment Compositions or combinations thereof. The hBNP peptide, hBNP fragment, or Human BNP Fragment Composition desirably can be labeled with any detectable label known to those skilled in the art, including those detectable labels discussed above in connection with the sandwich assay format. In this assay, optionally the antibody of the present invention can be immobilized on to a solid support using the techniques discussed previously herein. Alternatively, the antibody of the present invention desirably can be coupled to an antibody, such as an antispecies antibody, that has been immobilized on to a solid support, such as a microparticle.

The labeled hBNP, hBNP fragments, Human BNP Fragment Compositions, or combinations thereof, as well as the test sample and the antibody preferably are incubated under conditions similar to those described above in connection with the sandwich assay format. Two different species of antibody-hBNP complexes are then generated. Specifically, one of the antibody-hBNP complexes generated contains a detectable label while the other antibody-hBNP complex does not contain a detectable label. The antibody-hBNP complex can be, but does not have to be, separated from the remainder of the test sample prior to quantification of the detectable label. Regardless of whether the antibody-hBNP complex is separated from the remainder of the test sample, the amount of detectable label in the antibody-hBNP complex preferably is then quantified. The concentration of hBNP, hBNP fragments, Human BNP Fragment Compositions, or combinations thereof in the test sample can then be determined by comparing the quantity of detectable label in the antibody-hBNP complex to a standard curve. The standard curve can be generated using serial dilutions of hBNP, hBNP fragments, Human BNP Fragment Compositions, or combinations thereof of known concentration, by mass spectroscopy, gravimetrically and by other techniques known in the art.

The antibody-hBNP complex preferably can be separated from the test sample by binding the antibody to a solid support, such as the solid supports discussed above in connection with the sandwich assay format, and then optionally removing the remainder of the test sample from contact with the solid support.

The labeled hBNP, hBNP fragment, Human BNP Fragment Composition, or combinations thereof that is used to compete with hBNP, hBNP fragments, Human BNP Fragment Compositions, or combinations thereof in the test sample for binding to the antibody can be intact hBNP (1-32), any hBNP fragment, Human BNP Fragment Composition. or combinations thereof provided that the hBNP peptide (1-32), hBNP fragment, Human BNP Fragment Composition, or combinations thereof contain a sequence of amino acids that corresponds to an epitope that is recognized by the antibody. As discussed above, this includes minor sequence variations. One of ordinary skill in the art would know how to select variations that result in peptides or peptide fragments having acceptable functionality according to the invention, i.e., preferably an ability to compete with or substitute for hBNP, hBNP fragments, Human BNP Fragment Compositions, or combinations thereof in the test sample for binding to the antibody (as conferred by an ability to bind the antibody).

In a reverse competition assay, preferably an immobilized hBNP, a hBNP fragment, a Human BNP Fragment Composition, or combinations thereof can either be sequentially or simultaneously contacted with a test sample and at least one labeled antibody. Preferably, the antibody specifically binds to an epitope having an amino acid sequence comprising at least three (3) amino acids of the amino acid sequence of hBNP. An example of an antibody that can be used in such a reverse competition assay is an antibody as described in Section III, supra. The antibody optionally can be labeled with any detectable label known to those skilled in the art, including those detectable labels discussed above in connection with the sandwich assay format.

The hBNP peptide, hBNP fragment, Human BNP Fragment Composition, or combinations thereof optionally can be bound to a solid support, such as the solid supports discussed above in connection with the sandwich assay format.

The immobilized hBNP peptide, hBNP peptide fragment, Human BNP Fragment Composition or combinations thereof, as well as test sample and at least one labeled antibody preferably are incubated under conditions similar to those described above in connection with the sandwich assay format. Two different species hBNP-antibody complexes are then generated. Specifically, one of the hBNP-antibody complexes generated is immobilized and contains a detectable label while the other hBNP-antibody complex is not immobilized and contains a detectable label. The non-immobilized hBNP-antibody complex and the remainder of the test sample optionally are removed from the presence of the immobilized hBNP-antibody complex through techniques known in the art, such as washing. Once the non-immobilized hBNP antibody complex is removed, the amount of detectable label in the immobilized hBNP-antibody complex preferably is then quantified. The concentration of hBNP, hBNP fragment, Human BNP Fragment Composition, or combinations thereof in the test sample can then be determined, e.g., by comparing the quantity of detectable label in the hBNP-complex to a standard curve. The standard curve can be generated, for example, using serial dilutions of hBNP, hBNP fragment, Human BNP Fragment Composition, or combinations thereof of known concentration, by mass spectroscopy, gravimetrically and by other techniques known in the art.

In a fluorescence polarization assay, in one embodiment, preferably an antibody or functionally active fragment thereof is first contacted with an unlabeled test sample suspected of containing hBNP, a hBNP fragment, Human BNP Fragment Composition, or combinations thereof to form an unlabeled hBNP-antibody complex. The unlabeled hBNP-antibody complex is then optionally contacted with a fluorescently labeled hBNP, hBNP fragment, Human BNP Fragment Composition, or combinations thereof. The labeled hBNP, hBNP fragment, Human BNP Fragment Composition, or combinations thereof compete with any unlabeled hBNP, hBNP fragment, Human BNP Fragment Composition, or combinations thereof in the test sample for binding to the antibody or functionally active fragment thereof. The amount of labeled hBNP-antibody complex formed preferably is determined and the amount of hBNP, hBNP fragment, Human BNP Fragment Composition, or combinations thereof in the test sample optimally determined via use of a standard curve.

Preferably, the antibody used in a fluorescence polarization assay specifically binds to an epitope having an amino acid sequence comprising at least three (3) amino acids of hBNP. An example of an antibody that specifically binds to epitopes having an amino acid sequence containing at least three (3) amino acids of hBNP is an antibody described in Section III, supra. The antibody, labeled hBNP peptide, hBNP peptide fragment, Human BNP Fragment Composition, or combinations thereof and test sample and at least one labeled antibody preferably are incubated under conditions similar to those described above in connection with the sandwich assay format.

Alternatively, in another embodiment, preferably an antibody or functionally active fragment thereof is simultaneously contacted with a fluorescently labeled hBNP, hBNP fragment, Human BNP Fragment Composition, or combinations thereof and an unlabeled test sample suspected of containing hBNP, hBNP fragment, Human BNP Fragment Composition, or combinations thereof to form both labeled hBNP-antibody complexes and unlabeled hBNP-antibody complexes. The amount of labeled hBNP-antibody complex formed is optionally determined and the amount of hBNP in the test sample determined, e.g., via use of a standard curve. The antibody used in this immunoassay preferably specifically binds to an epitope having an amino acid sequence comprising at least three (3) amino acids of the amino acid sequence of hBNP. An example of an antibody that specifically binds to epitopes having an amino acid sequence containing at least three (3) amino acids of hBNP is an antibody produced as described in Section III, supra.

Alternatively, in yet another embodiment, an antibody (such as antibody of the present invention, such as an antibody described in Section III) or functionally active fragment thereof preferably is first contacted with a fluorescently labeled hBNP, hBNP fragment, Human BNP Fragment Composition, or combinations thereof to form a labeled hBNP-antibody complex. The labeled BNP-antibody complex is then preferably contacted with an unlabeled test sample suspected of containing hBNP, a hBNP fragment, a Human BNP Fragment Composition, or combinations thereof. Any unlabeled hBNP, hBNP fragment Human BNP Fragment Composition, or combinations thereof in the test sample compete with the labeled hBNP, hBNP fragment, Human BNP Fragment Composition or combinations thereof for binding to the antibody or functionally active fragment thereof. The amount of labeled hBNP-antibody complex formed is then optionally determined and the amount of hBNP in the test sample determined, e.g., via use of a standard curve. The antibody used in this immunoassay preferably specifically binds to an epitope having an amino acid sequence comprising at least three (3) amino acids of hBNP. An example of an antibody that specifically binds to epitopes having an amino acid sequence containing at least three (3) amino acids of hBNP an antibody described in Section III, supra.

Now by way of example, and not of limitation, examples of the present invention shall now be given.

EXAMPLE 1

Sample Collection

EDTA plasma of healthy human subjects and human BNP plasma specimens were obtained from ProMedDx LLC (Norton, Mass.), shipped on dry ice, and stored at −70° C. before use. Human BNP concentrations of all human BNP clinical specimens were above 1000 pg/mL based on Bayer Centaur BNP assay (Bayer, Germany).

EXAMPLE 2

Identification of Human BNP Fragments Using MALDI-tof-MS

Identification of human BNP molecular forms was initially carried out by MALDI analysis of immunomagnetic separated human BNP degradation products derived from spiked human BNP in normal human EDTA plasma. Anti-human BNP monoclonal antibody ("mAb") 106.3 (Scios, Fremont, Calif.) targeting the N-terminus (epitope 5-13) was coated on carboxy paramagnetic microparticles ("mµP"), and used to capture human BNP fragments.

The mµP (Polymer Laboratories, Amherst, Mass., 4.7 µm) was coated with anti-BNP 106.3 mAb via EDAC coupling chemistry (EDAC: 1-[3-(dimethylamino)propyl]-3-ethylcarbodiimide hydrochloride). Briefly, 8 mL mµP at 5% solids was added to a 50 mL conical centrifuge tube. The mµP were captured with a magnetic separator (SPHERO UltraMag Separator) (4 min) and the supernatant removed. The mµP was resuspended in 25 mL MES buffer, pH 5.5, placed on a tube rotator (Scientific Equipment Products, Baltimore, Md., Cat. No. 60448) for 3-4 min, then captured with a magnetic separator (SPHERO UltraMag Separator) for 3 min. The MES wash/capture cycles were repeated for a total of 4 times. The washed particles were resuspended in 30.65 mL of 25 mM MES buffer, and reacted with 0.95 mL of 2.1 mg/mL anti-human BNP 106.3 and 0.40 mL of 20 mg/mL EDAC, then were placed on rotator for 45 minutes. The mAb 106.3 coated mµP were then captured (4 min) with a magnet (supernatant removed), washed in 40 mL of 0.1% Tween20/PBS buffer 3 times, then BSA-overcoated by resuspending the coated mµP in 40 mL of 1% BSA/PBS buffer on rotator for 40 min. The coated mµP was then captured (4 min) with a magnet (supernatant removed), washed 3 times in 0.1% Tween 20/PBS buffer, and resuspended in 40 mL mµP diluent containing BSA, Tris buffer (pH 8.0), antimicrobial and other stabilizer (1% solid).

Human BNP was spiked into pooled EDTA plasma of healthy human subjects to a final concentration of 4 µg/mL by adding 40 µl of human BNP 1-32 (1 mg/mL) in water to an Eppendorf vial containing 960 µl of pooled EDTA plasma. The spiked solutions were allowed to incubate at room temperature for 1, 4 and 24 hours. Human BNP fragments were extracted as follows: 50 µL aliquots were then removed at each time point (1, 4, 24 hours) and placed into a 2.0 mL microcentrifuge tube containing 25 µL of anti-human BNP 106.3 coated microparticles and allowed to incubate for 30 minutes at room temperature. After incubation, the tubes were placed into a magnetic rack (SPHERO FlexiMag Separator Junior, from Spherotech, Libertyville, Ill.) in order to separate the magnetic microparticles from the plasma. The plasma was removed and the microparticles were washed with 50 µL of HPLC grade water. The washing included removing the centrifuge tube from rack, resuspending the microparticles in the water, and finally placing the centrifuge tube back on the rack to separate the microparticles and remove the water. After the wash, human BNP and human BNP fragments were released by resuspending the microparticles in 25 µL MALDI matrix, a-cyano-4-hydroxycinnamic acid in 2/1 (v/v) acetonitrile/0.3% TFA, at room temperature for 5 minutes. After incubation with MALDI matrix, the microparticles were separated from the matrix using the magnetic rack and 1 µL of MALDI matrix sample was spotted onto the target for MALDI analysis according to manufacturer's protocol. Each sample is interrogated by an UV laser and the resulting ions were analyzed by MALDI-tof-MS. Peptide identification is obtained by matching an observed m/z value to a predicted molecular mass.

Figure 3:
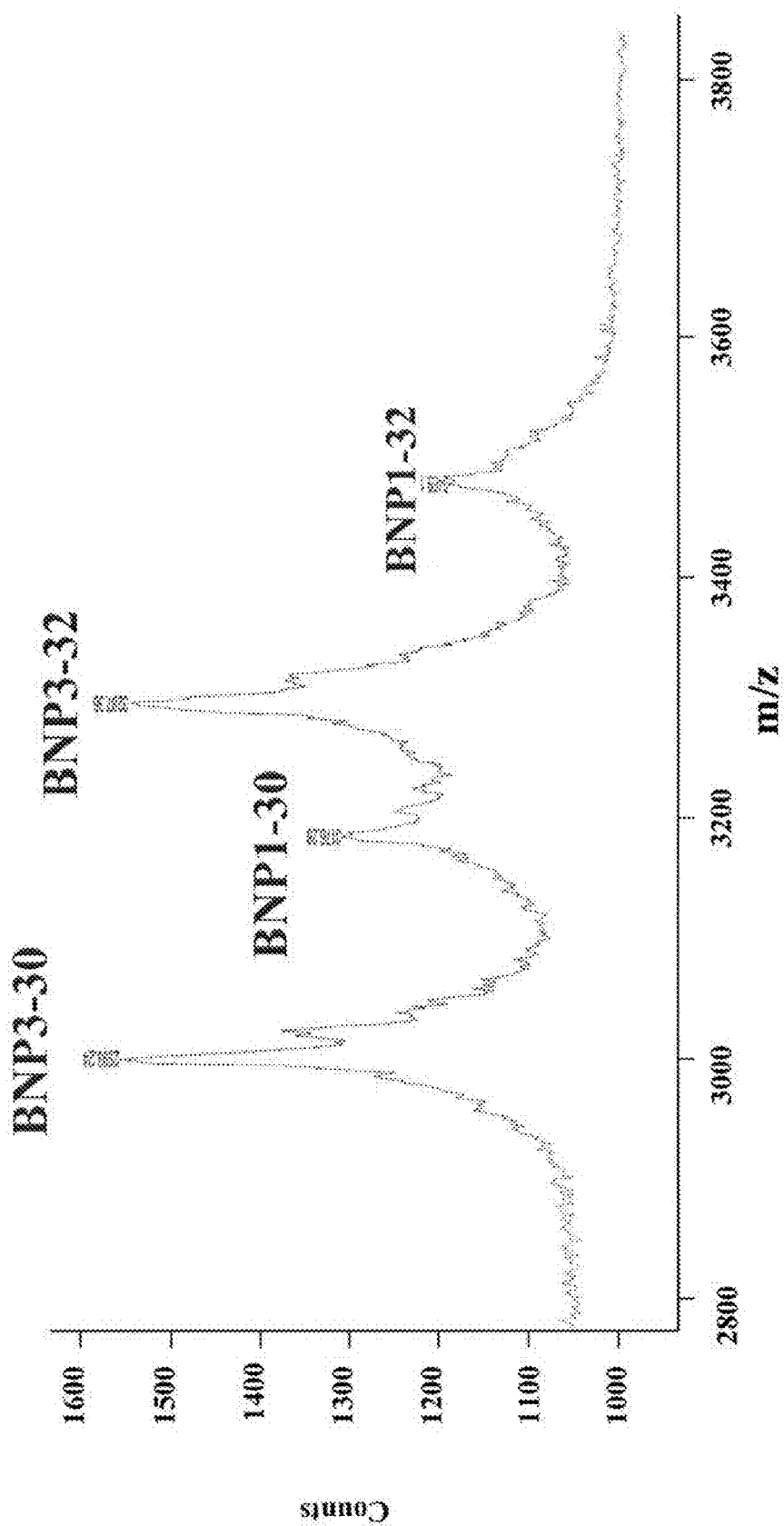
FIG. 3 shows a typical MALDI spectrum of human BNP degradation observed at time of approximately 30 minutes, evidencing the following human BNP fragments were identified in spiked plasma samples, human BNP fragments: 1-30 ("BNP1-30"); 3-30 ("BNP3-30"); 3-32 ("BNP3-32"); and 1-32 ("BNP1-32").

The following human BNP fragments were identified in spiked plasma samples: human BNP fragments 1-30, 3-30, 3-32 and 1-32 (See, FIG. 3). In addition, ions at m/z value 16-18 greater than human BNP fragment 3-30 were also observed.

EXAMPLE 3

Identification of Human BNP Fragments Using LC/MS

To study human BNP fragments with enhanced resolution, API QSTAR PULSARi (Applied Biosystems, Foster City, Calif.) instrument was utilized. Following incubation of human BNP 1-32 spiked in EDTA plasma of healthy human subjects (40 µg/mL) at room temperature for 24 hours, human BNP fragments were extracted as described in Example 2 and analyzed by LC/MS. A Magic C18 column (5 um, 100 Å, 0.3×150 mm) from Michrom BioResource, Inc. (Auburn, Calif.) was used for the separation. Mobile phase A contains 2/97.9/0.1 (v/v/v) acetonitrile/water/formic acid. Mobile phase B contains 97.9/2/0.1 acetonitrile/water/formic acid. The flow rate was 10 µl/min, with B ramped from 0 to 30% over 50 minutes followed by 30% to 50% over 80 minutes to separate captured human BNP degradation products and their reduction products.

Two major human BNP fragments were observed. One is human BNP fragment 3-30 with m/z 995.7144 (monoisotopic mass). The other one is a more abundant human BNP fragment observed as triply charged ions at m/z 1001.7191 (See, FIG. 4), corresponding to a human BNP fragment that is 18 mass unit heavier than human BNP fragment 3-30. This corresponds to a cleavage on the human BNP ring, with the formation of cross-linked human BNP fragments, which exhibit an X-shape, namely, human BNP fragment 3-30x, which is also referred to herein as a BNP Fragment Composition.

EXAMPLE 4

Determination of the Sites of Cleavage on the Human BNP Fragment 3-30X by LC/MS

Figure 4:
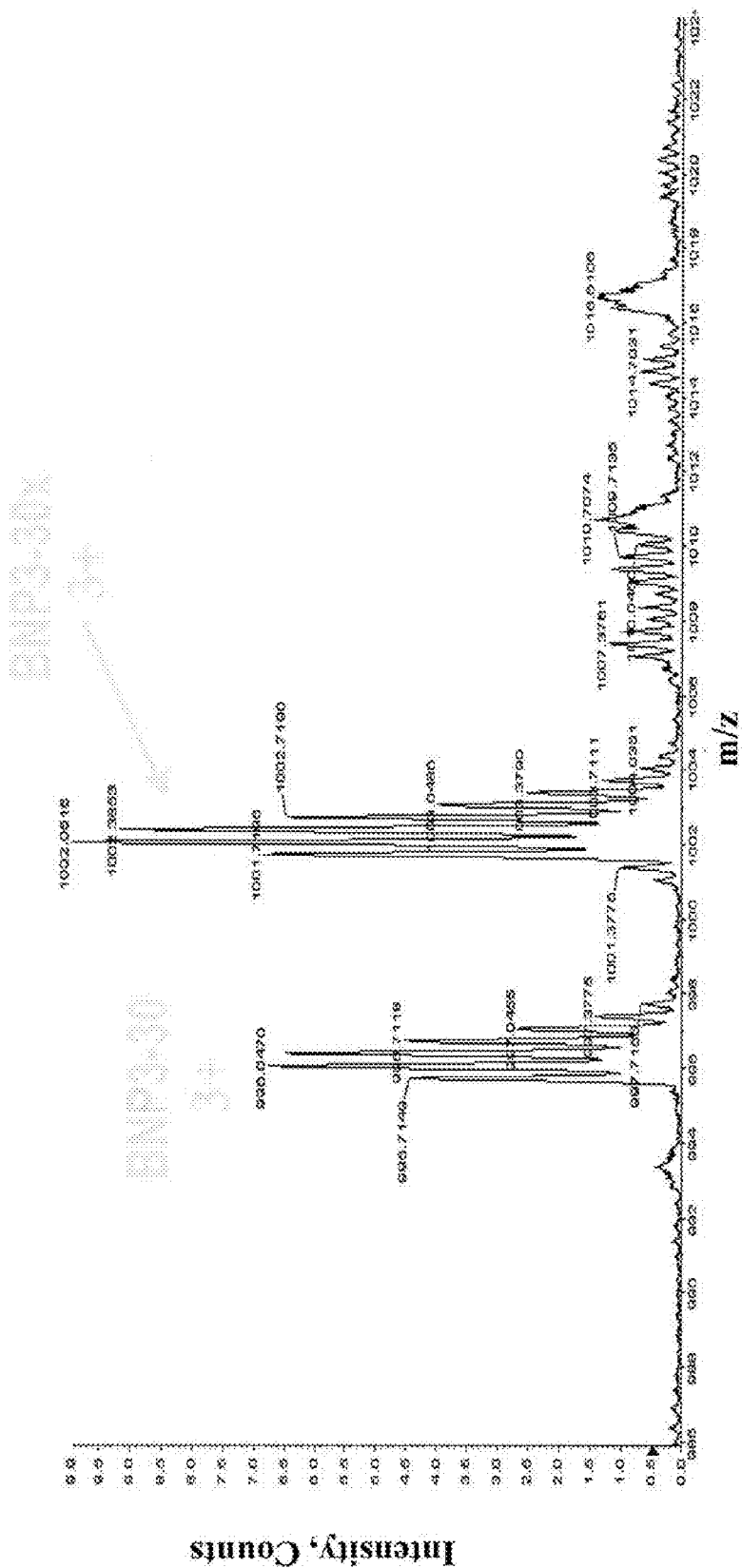
FIG. 4 shows the determination of the presence of human BNP ring cleavage products. Human BNP 1-32 was spiked in pooled human EDTA plasma at 40 mg/mL, incubated at room temperature for 24 hours. The degradation products were captured by monoclonal antibody-coated magnetic particles and analyzed by LC/MS by QSTAR PULSARi. The major degradation products are identified as human BNP fragment 3-30 ("BNP3-30"), and the Human BNP Fragment Composition (defined hereinafter), 3-30x ("BNP3-30x"; the 'x' referring to the fact that the 2 human BNP fragments are cross-linked) with ring cleavage(s). Oxidation products of the two major species are also present in the spectrum, along with $Na^+$ and $K^+$ adducts.
Figure 6:
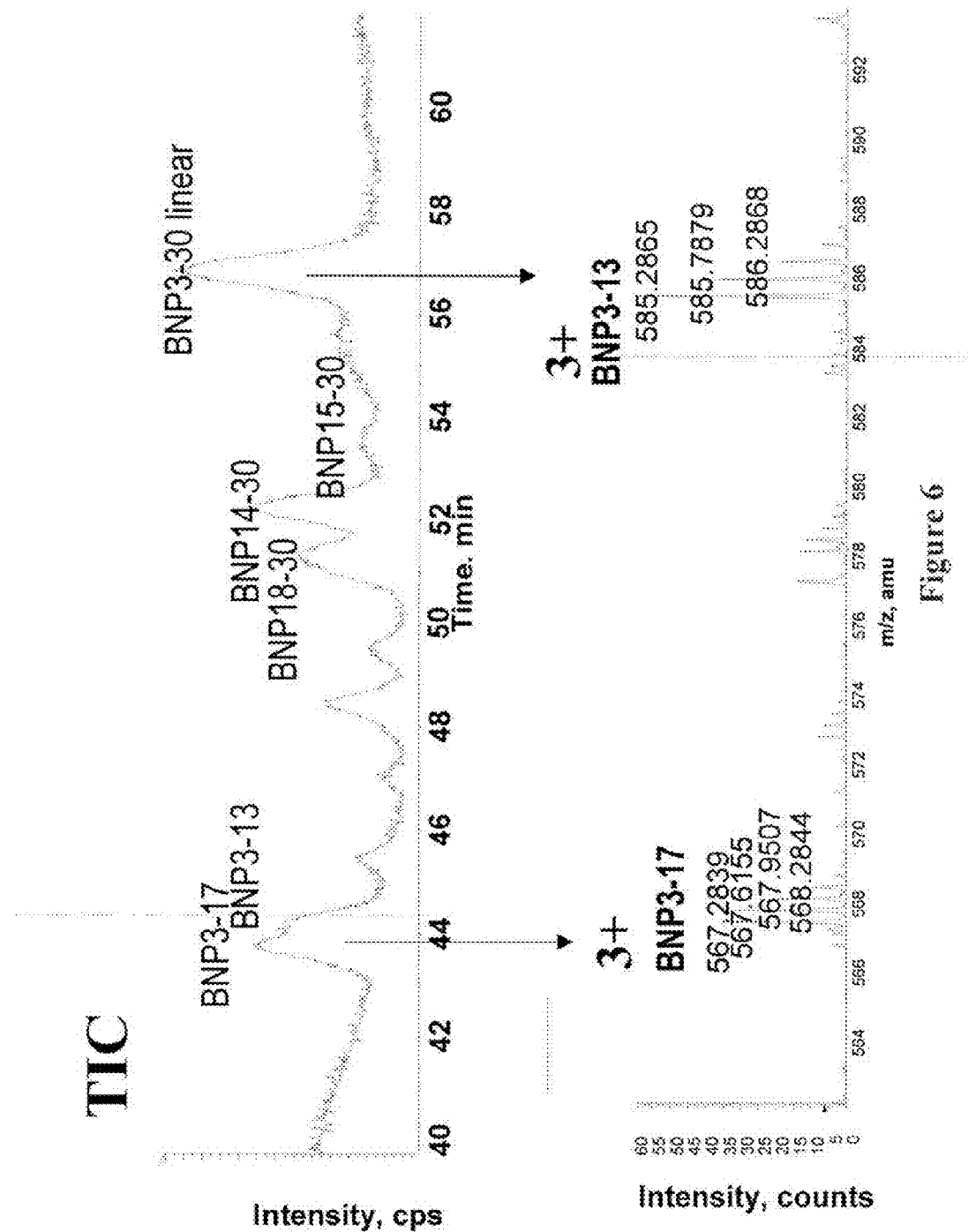
FIG. 6 provides the total ion chromatogram (top panel) and a MS spectrum (lower panel) of LC/MS analysis of the TCEP-reduced degradation products for the determination of cleavage sites by LC/MS of reduced human BNP degradation products (e.g., human BNP fragments, "BNP3-17", "BNP3-13", "BNP14-30", "BNP15-30", and "BNP18-30"), with resolution of the BNP3-17 and BNP3-13 shown. Gradient; flow rate; solvents are as described in the Examples.

The sites of cleavage on the human BNP ring of human BNP fragments 3-30x were investigated. The mixture of human BNP fragments 3-30 and human BNP fragments 3-30x in Example 2 was then reduced by a 5 mM Tris (2-carboxyethyl)phosphine ("TCEP") from Pierce (Rockford, Ill.) for 10 minutes. Peptides indicative of the cleavage sites were produced (See, FIG. 5). As shown in FIG. 4, the captured human BNP fragments before TCEP reduction contain human BNP fragments 3-30 and human BNP fragments 3-30x. After TCEP reaction, the samples were analyzed by LC/MS using same procedure as described in Example 3. Since each X-shaped human BNP fragment produces 2 peptides following reduction, the mass of observed peptides were compared with those calculated from ring-cleavage products of human BNP fragment 3-30x. Using this approach, four human BNP fragments were identified, namely, human BNP fragments, 3-13, 14-30, 15-30, 3-17 and 18-30 (See, FIG. 6 and Table 1, below). Therefore, the three cleavage sites on the ring are Arg13, Lys14 and Arg17. The results further confirmed the proteolytic cleavage of human BNP ring.

TABLE 1

| BNP Fragment | Monoisotopic mass (calculated) | Monoisotopic mass (measured) |
| --- | --- | --- |
| BNP3-13 | 1168.55 | 1168.53 |
| BNP14-30 | 1835.97 | 1835.91 |
| BNP3-17 | 1698.81 | 1698.84 |
| BNP18-30 | 1305.71 | 1305.74 |
| BNP15-30 | 1707.88 | 1707.91 |

EXAMPLE 5

Determination of the Human BNP fragments from Human BNP 1-32 Spiked in EDTA Plasma of Healthy Subjects Using API4000

To study human BNP degradation near physiological concentration, an API4000 LC/MS system (Applied Biosystems, Foster City, Calif.) equipped with Agilent 1100 HPLC was used to determine the degradation of human BNP spiked at 5 ng/mL in a pooled normal EDTA plasma. The sample was extracted with the same procedure as in Example 2 except that 1 mL of EDTA plasma sample and 200 µl microparticles (0.1% solid) were used for the extraction. The major human BNP degradation products (namely, 1-32, 3-32, 3-30, and 3-30x) and kinetics were analyzed by LC/MS using selected ion monitoring mode according to instrument protocol. Phenomenex Luna C18 column (2×250 mm, 5 micron, 100 Å) was used for the separation. Mobile phase A consisted of 980/20/1.5/0.9 (v/v/v/v) water/acetonitrile/trifluoacetic acid. Mobile phase B consisted of 20/980/1.5/0.9 (v/v/v/v) water/acetonitrile/trifluoacetic acid. The percentage B was ramped from 20% to 80% in 15 minutes at 250 µl/min.

Figure 7:
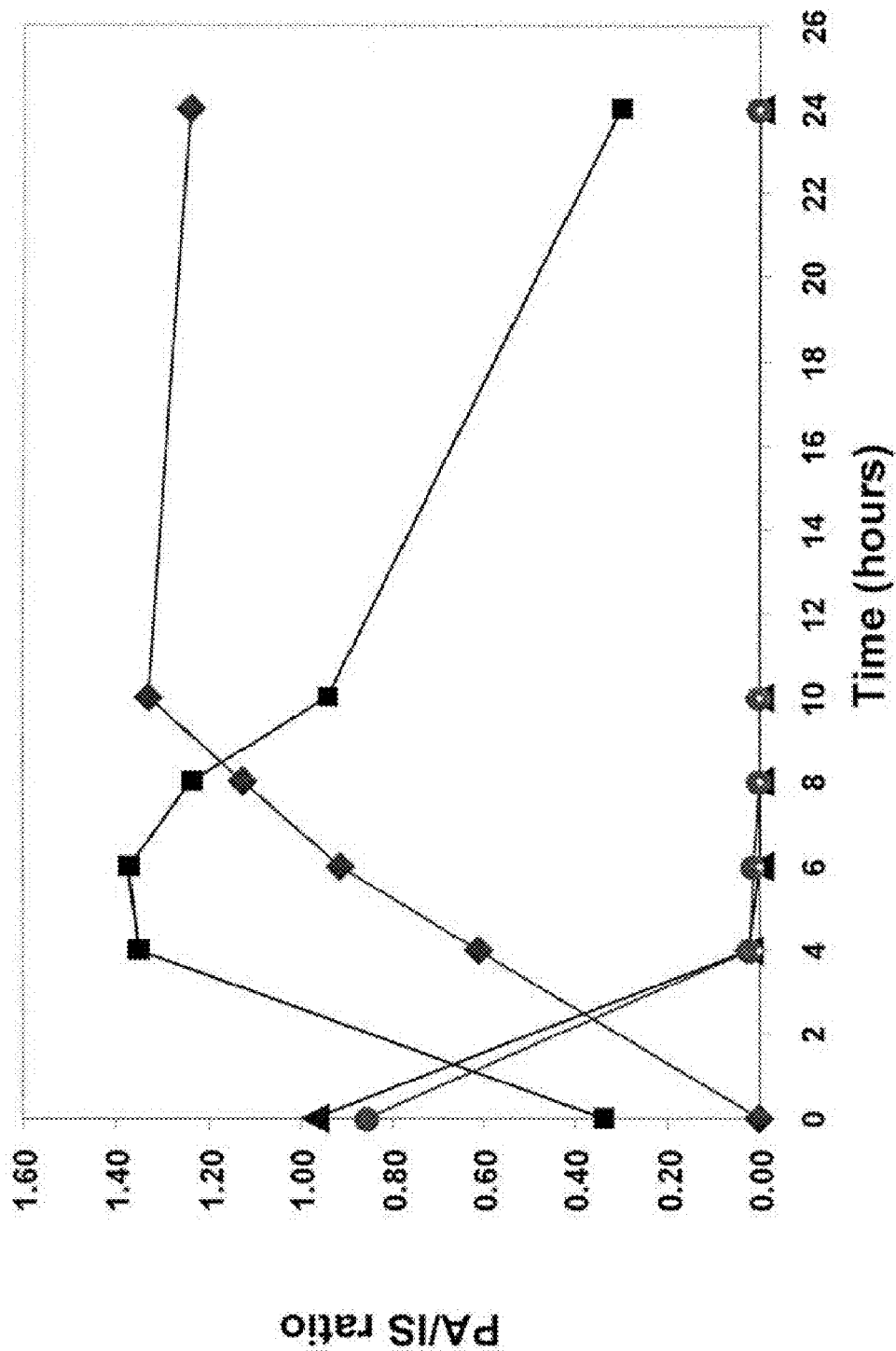
FIG. 7 shows the results of a time-course (kinetics) study on human BNP degradation: human BNP was spiked into normal human EDTA plasma at room temperature to 5 ng/mL. An aliquot of the mixture was taken at various time points with protease inhibitor added and frozen immediately. Samples were extracted along with an internal standard (the internal standard was a biotinylated human BNP mutant. In this mutant, amino acid 32 (histidine) was replaced by alanine and is hereinafter referred to as "Biotin-BNP1-32 (H32A)") by a monoclonal antibody 106.3 (hereinafter referred to as "mAb 106.3") coated magnetic microparticles and released human BNP and fragments were analyzed by LC/MS. The relative abundance of each fragments were plotted. Symbols: —▲—refers to human BNP fragment 1-32, —●—refers to human BNP fragment 3-32, —■—refers to human BNP fragment 3-30, and —♦—refers to human BNP fragment 3-30x.

The relative concentration of human BNP fragments 3-32, 3-30 and 3-30x were monitored at various time points (0.5, 4, 6, 8, 10, 24 hours). Triply charged human BNP peptides and human BNP fragments, namely, 1-32, 3-32, 3-30, and 3-30x were monitored at m/z 1155.6, 1094.6. 996.5 and 1002.5, respectively. As shown in FIG. 7, the concentration of human BNP 1-32 (solid triangles) and human BNP fragment 3-32 (solid circles) decreased drastically over the time course of study; the concentration of human BNP fragment 3-30 (solid squares) went up, reaches a peak, then drops thereafter; the concentration of human BNP fragment 3-30x (solid diamonds) goes up and then appears relatively flat over time. The kinetics of the reactions is consistent with these species as the starting material, intermediate and final product. The results demonstrated that the LC/MS method is suitable for monitoring the degradation products at physiological concentrations.

EXAMPLE 6

Determination of the Human BNP Fragments from Human BNP 1-32 Spiked in EDTA Plasma of Heart-Failure Patients Using API 4000

Human BNP was spiked into Human BNP specimens (EDTA plasma) using the same procedure as in Example 2, and the spiked samples were studied using the same methodology as in Example 4. It was found that those spiked samples revealed similar proteolytic degradation patterns as observed for human BNP spiked in pooled human EDTA plasma of healthy human subjects, with loss of the N-terminal SP and Arg-C type of cleavage at the C-terminus and cleavages on the human BNP ring. However, the cleavage rates appeared to be slower in the heart-failure patient samples: after 8 hours incubation at the room temperature, 80% of the degradation products still contain the C-terminus (human BNP fragment 3-32, human BNP 1-32, and human BNP fragments 3-32X and 1-32x). When the same concentration of human BNP was spiked into a pooled EDTA plasma of healthy human subjects, only 5% of the fragments contain intact C-terminus after 4 hours incubation at room temperature (See, Example 5).

EXAMPLE 7

Determination of Human BNP Fragments from Heart-Failure Patient Plasma Samples

In this study, human BNP degradation products in human BNP specimens and the impact of temperature on degradation was studied. Prior to sample extractions for analysis, each sample was split into two vials and incubated at room temperature for 0 hours (t=0 hour) and 48 hours (t=48 hours), respectively. The samples were then extracted using the methodology described in Example 4 and analyzed by the API 4000.

Human BNP specimens were initially analyzed by monitoring typical human BNP fragments (namely 1-32, 3-30, 3-30x, 3-32) observed from spiked human BNP using the methodology described in Example 4. No apparent signals from those human BNP fragments were detected from samples with high concentrations of human BNP (1000-5000 pg/mL) as measured by immunoassay, indicating that the human BNP fragments are different from what were observed from human BNP spiked in EDTA plasma. This result suggested that there are other enzymes involved in degradation of human BNP besides proteases such as DPP IV and the Arg-C type of enzymes.

To identify proteolytic degradation products, exoproteases such as aminopeptidase, and endoprotease such as Arg-C, were initially presumed to be the cause of degradation. Since most commercial human BNP assays employ antibodies targeting the C-terminus of the human BNP 1-32, it was assumed that the C-terminus is relatively stable compared with the N-terminus. This is consistent with the results described in U.S. Patent Publication US2005/0064511 A1.

To further ensure that the correct fragments were being monitored, mixtures of human BNP fragments (namely, human BNP fragments n-32 and BNP n-32x, with n being an integer from =1 to 6) were prepared using enzymatic cleavage by aminopeptidase and subsequently cleaved by endoprotease Arg-C in 20 mM ammonium bicarbonate using the manufacturer suggested enzyme/substrate ratio. The fragment formation was monitored by MALDI-tof-MS, and the fragments were then analyzed by the same LC/MS procedure described in Example 4 as standards to determine the retention time of each fragment.

Figure 8A:
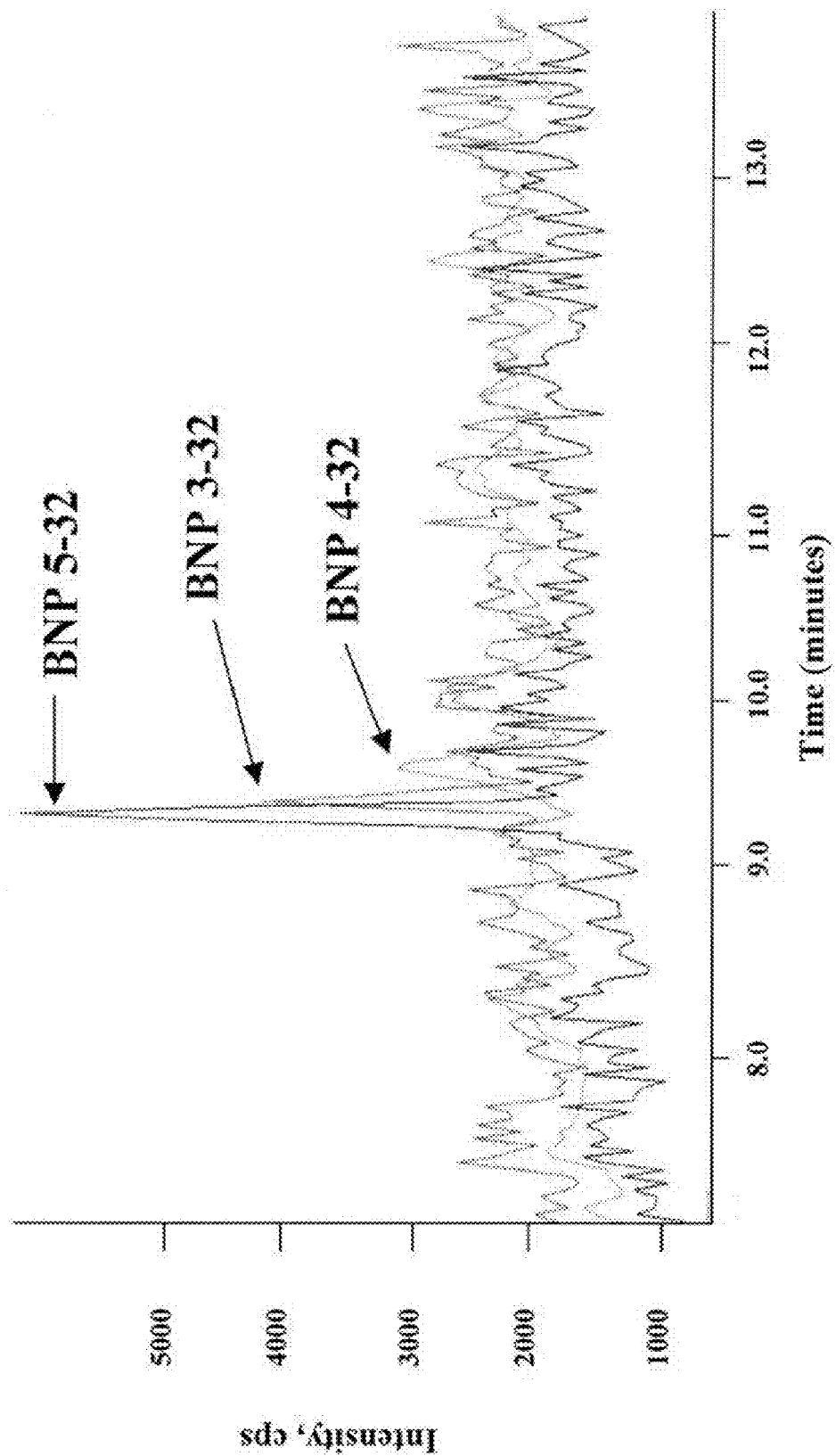
FIGS. 8a and 8b show human BNP fragments identified in human BNP specimen before and after incubation at room temperature at either time T=0 (FIG. 8a) or at time T=48 hours (FIG. 8b). At time T=0 (FIG. 8a), hBNP fragments 5-32, 3-32, and 4-32 were observed. At time T=48 hours (FIG. 8b), the Human BNP Fragment Composition (defined hereinafter) 5-30x ("BNP5-30x") and 5-30 ("BNP5-30") were observed.
Figure 8B:
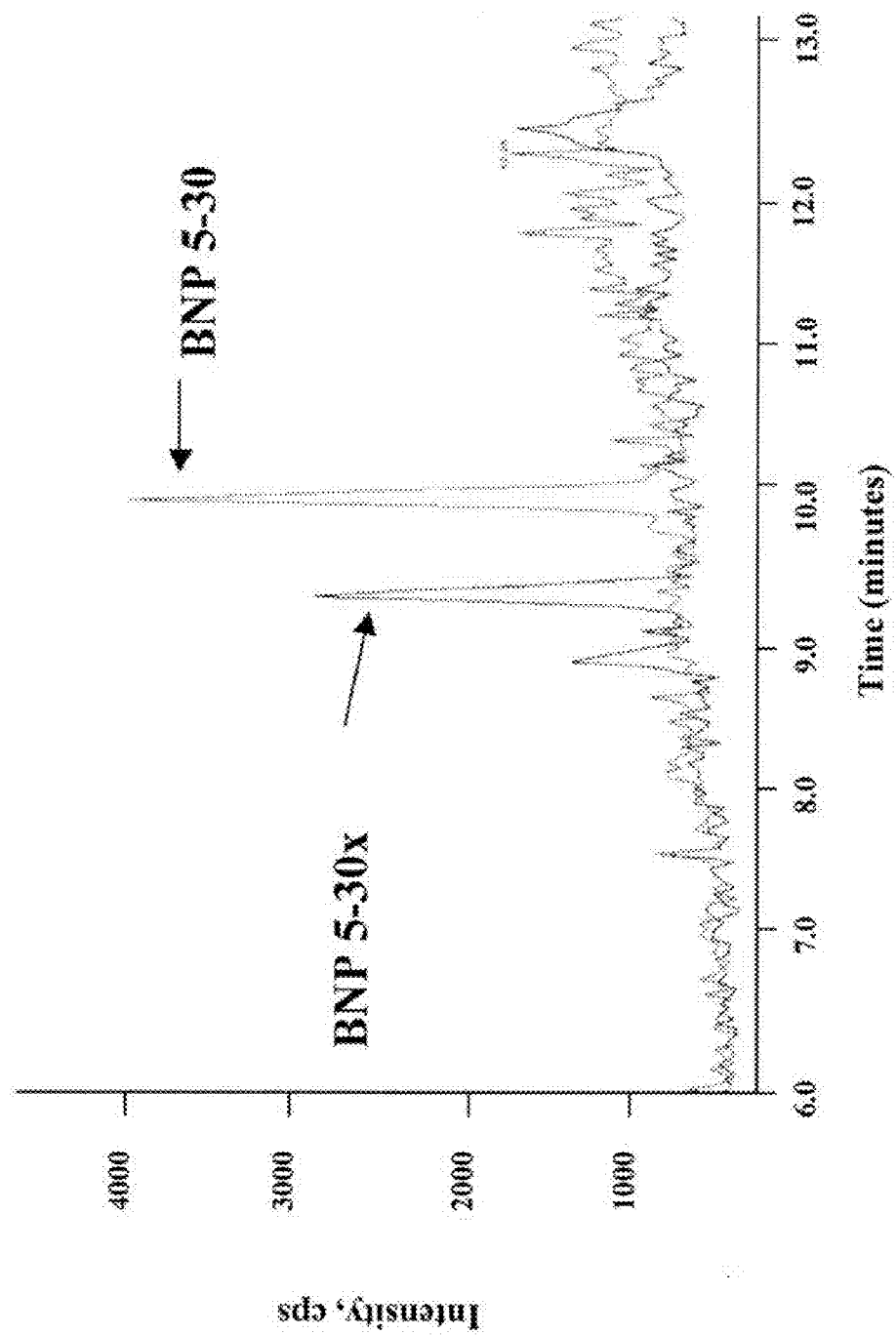
Figure 9A:
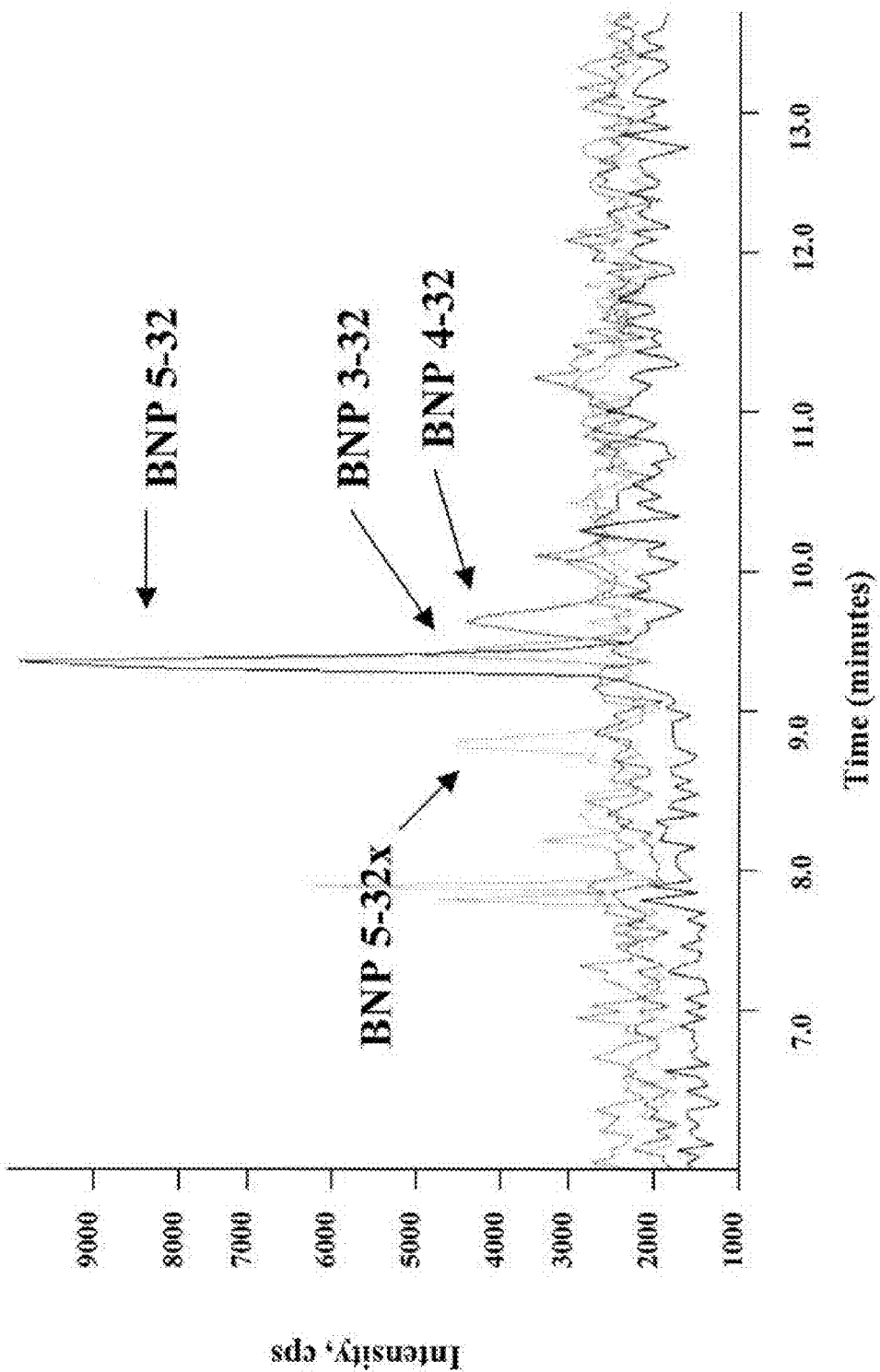
FIGS. 9a and 9b show human BNP fragment identified in human BNP specimen before and after incubation at room temperature. At time T=0 (FIG. 9a), hBNP fragments 5-32, 3-32, 4-32 and 5-32x were observed. At time T=48 hours (FIG. 9b), only the Human BNP Fragment Composition (defined hereinafter) 5-30x ("BNP5-30x") was observed.
Figure 9B:
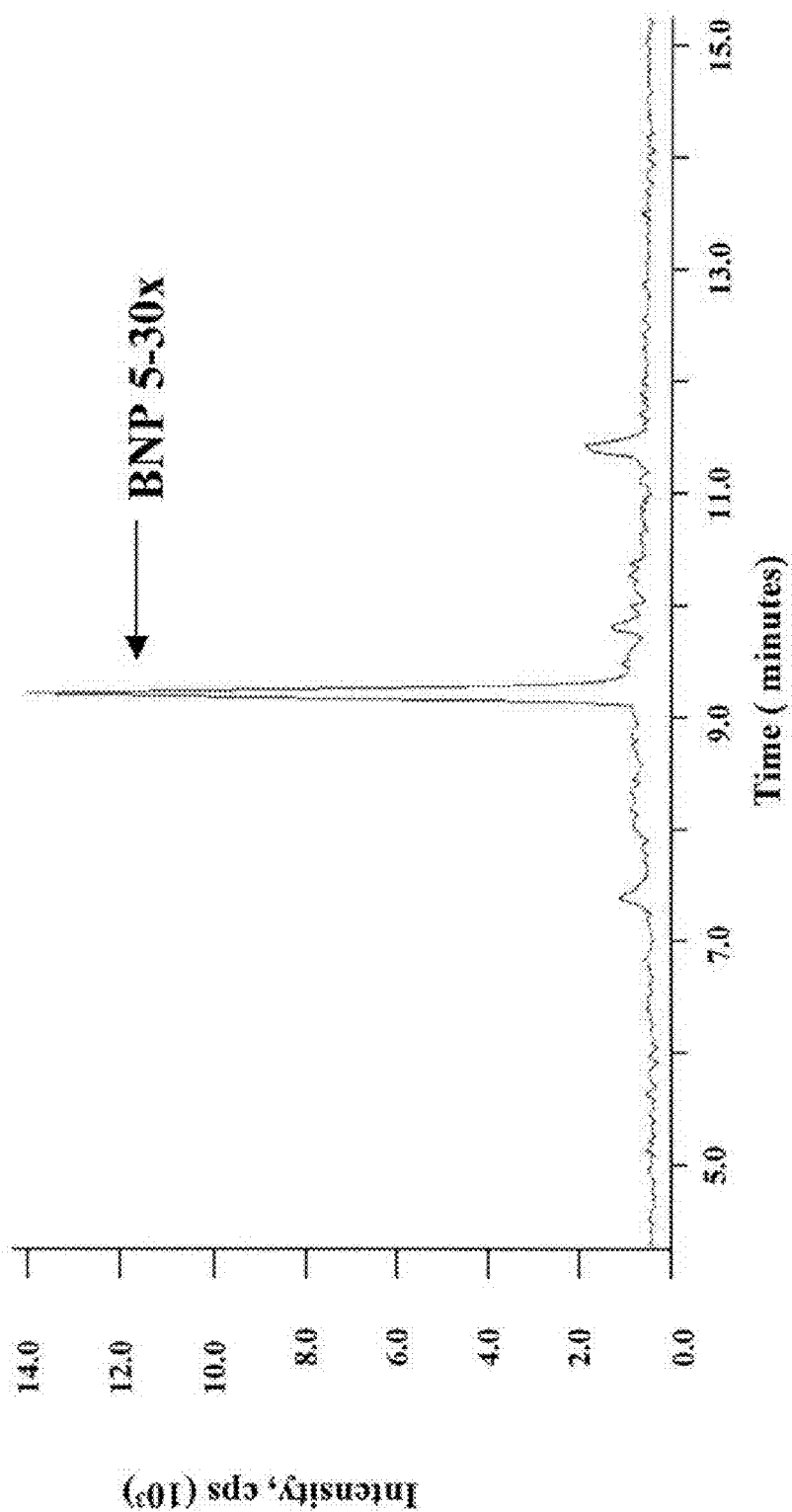
Figure 10A:
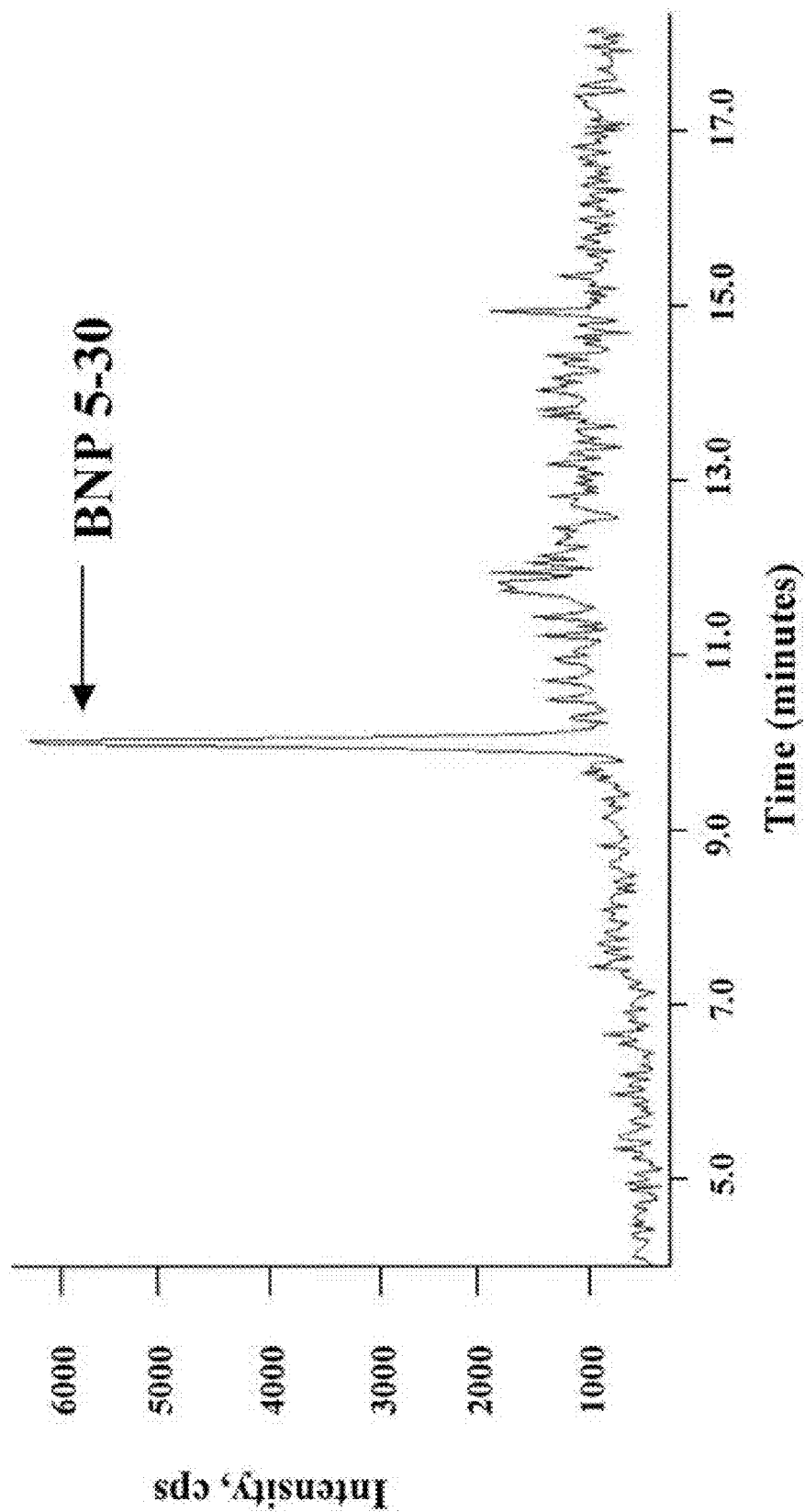
FIGS. 10a and 10b show human BNP fragments identified in a human BNP specimen before and after incubation at room temperature. At time T=0 (FIG. 10a), hBNP fragment 5-30 was observed. At time T=48 hours (FIG. 10b), only the Human BNP Fragment Composition (defined hereinafter) 5-30x ("BNP5-30x") was observed.
Figure 10B:
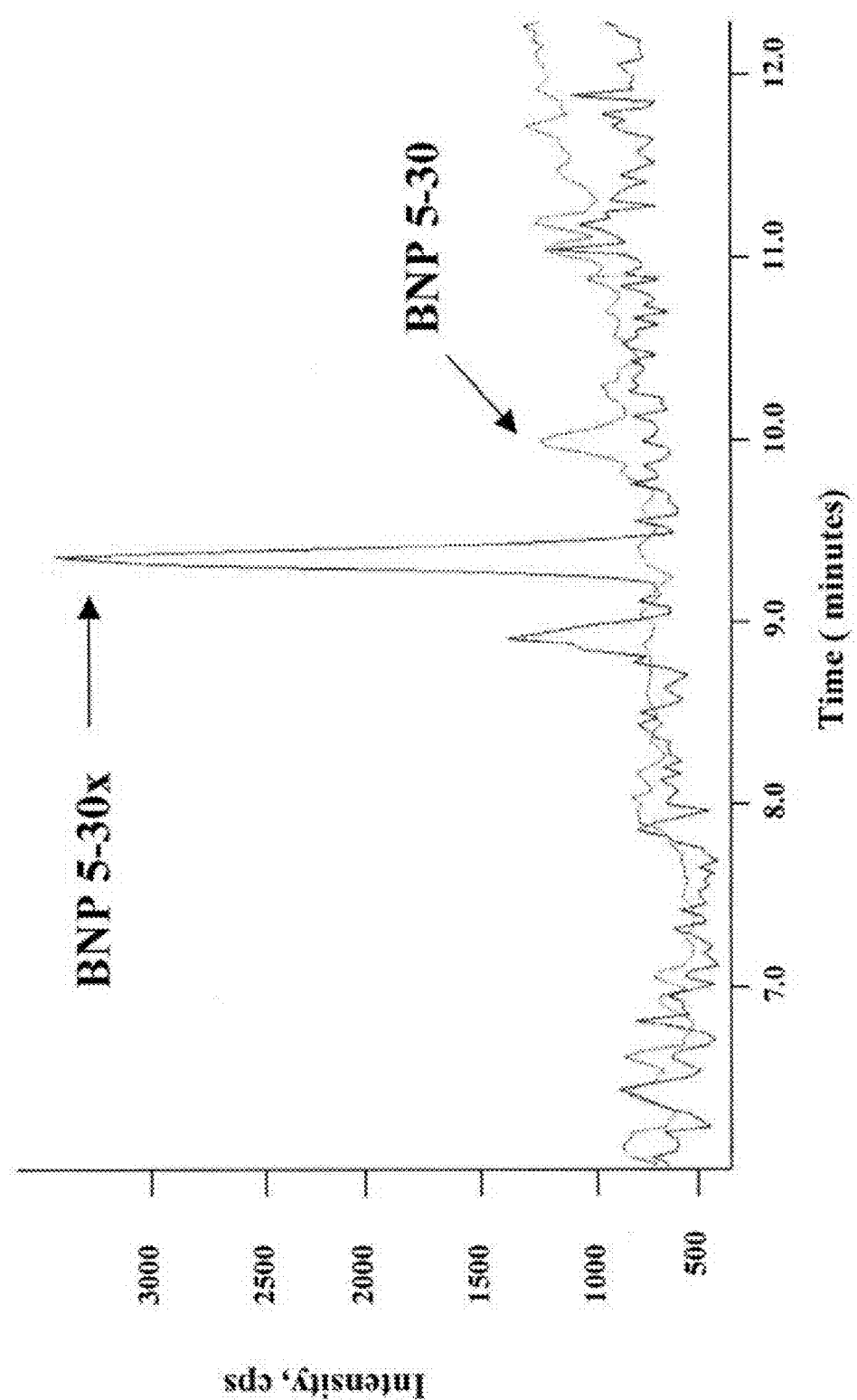

Experiments were conducted to determine if human BNP n-32 fragments (where n is an interger b=1, 2, 3, 4, 5, 6) were present in the specimen and to evaluate whether aminopeptidase type protease is involved in human BNP degradation. The samples were prepared and analyzed using the same methodology as described in Example 4, except that samples were monitored for human BNP n-32 fragments (n=1, 2, 3, 4, 5, 6, 7). As shown in FIGS. 8a and 9b, human BNP fragments 5-32, 4-32 and 3-32 were repeatedly detected. Human BNP fragment 5-32 was typically the most abundant fragment detected. Human BNP fragment 5-32x (FIG. 9a) and 5-30 (FIG. 10a) were also found in serum samples Next, to determine if ring cleavage products were present, human BNP fragment 5-32x was then monitored prior to and after incubation at room temperature. The samples were not monitored for other human BNP n-32x fragments since these fragments would be formed by the same process as human BNP 5-32x fragments. Additionally, monitoring for more fragments would reduce the detection sensitivity of the method. As shown in FIGS. 8b and 10b, cleavage products BNP 5-32x fragments become the major product at T=48 hours. In FIG. 9b, BNP5-32 is observed before incubation, and becomes more prominent after incubation at room temperature for 48 hours.

Using both of these approaches, human BNP fragments prior to and after room temperature incubation were monitored for both human BNP n-32 fragments and human BNP n-32x fragments for 20 samples. As shown in Table 2a, below, prior to room temperature incubation (t=0) most patient samples were found to contain intact C-termini (namely, human BNP fragments 5-32, 4-32, 3-32); a few patients had human BNP fragments, 5-32x.

After 48-hour room temperature incubation, further degradation products from the major human BNP fragment 5-32 were found to be human BNP fragments 5-30 and 5-30x due to the same Arg-C type of cleavages (See FIGS. 8b, 9b and 10b). Table 2b, below, summarizes the results of analysis of twenty human BNP specimens, with numbers in the table indicating peak height ranking (1 is the highest peak, 2 is the second highest peak). The results further confirmed the degradation of Arg-C type degradation at the C-terminus and on the human BNP ring.

In summary, patient samples contains mostly human BNP fragments 5-32, 3-32, 4-32. The samples also contain human BNP fragments, n-32x and n-30x.

TABLE 2a

Human BNP fragment Peak high ranking (T = 0 hours)

| | T = 0 Sample # | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| 1-32 | | | | | | | | | 3 | | | | | | | | | | | |
| 3-32 | *2 | 2 | | 3 | 2 | | 2 | | 4 | | 2 | 2 | | 2 | 2 | 2 | 2 | 2 | 3 | |
| 3-30 | | | 3 | | | 3 | | 2 | | | | 5 | 2 | | | | | | | |
| 3-30x | | | | | | | | | | | | | 5 | | | | | | | |
| 4-32 | 3 | | | 2 | 3 | | 3 | | 2 | | | | 3 | | 3 | 3 | 3 | 3 | 3 | 4 |
| 4-30 | | | 2 | | | 2 | | 3 | | | | | 3 | | | | | | | |
| 5-32 | 1 | 1 | | 1 | 1 | | 1 | | 1 | 1 | | 1 | | 1 | 1 | 1 | 1 | 1 | 2 | 1 |
| 5-32x | | | | | 4 | | 4 | | | | 2 | 6 | | | | | | | | |
| 5-30 | 4 | | 1 | | | 1 | | 1 | | | 1 | 4 | 1 | | 4 | 4 | 4 | 1 | | |
| 5-30x | | | | | | | | | | | | | 4 | | | | | | | |

TABLE 2b

Human BNP fragment Peak high ranking (T = 48 hours)

| | T = 48 Sample # | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| 5-32 | 2 | | | 1 | 2 | | N/A | | 3 | N/A | | | | | | | | | | |
| 5-32x | | | | | | | N/A | | | N/A | | | | | | | | | | |
| 5-30 | 1 | 2 | 2 | 2 | 1 | 2 | N/A | 2 | 1 | N/A | 1 | 1 | 2 | 1 | 1 | 1 | 1 | 2 | 2 | 1 |
| 5-30x | 3 | 1 | 1 | 3 | 3 | 1 | N/A | 1 | 2 | N/A | 2 | 2 | 1 | 2 | 2 | 2 | 2 | 1 | 1 | 2 |

EXAMPLE 8

Chemical Degradation of Human BNP

Human BNP (1-32) can be chemically degraded at specific amino acids. Human BNP (1-32) (50 mg, synthetic) was dissolved in 5 mL of 3% trifluoroacetic solution in 30% aqueous acetonitrile. Cyanogen bromide 15 mg as a solution in 1 mL of acetonitrile was added to the human BNP solution. The mixture was incubated for 16 hrs at room temperature. Cyanogen bromide cleaves human BNP at amino acids 4 and 16 giving rise to two peptides. The first human BNP fragment contained amino acids 4-16 of human BNP and the second human BNP fragment contained amino acids 17-32. The first human BNP fragment and the second human BNP fragment were cross-linked by a disulfide bond between the cysteine at amino acid 10 in the first human BNP fragment and the cysteine at amino acid 26 in the second human BNP fragment. These cross-linked human BNP peptides were isolated by reverse phase HPLC ("RP-HPLC") purification on a Luna C18 (2) semipreparative column (Phenomenex, Torrance, Calif.). The sample was injected on Luna C18 (2) (10×250 mm) that was preequilibrated at 10% acetonitrile in 0.1% aqueous TFA, for 15-20 min. The sample was injected and the peptide eluted with a gradient of 10-40% acetonitrile in 0.1% aqueous TFA over 60 min. The peptide elutes around 35-40 min at a flow rate of 5 mL/min. The peptide fractions were analyzed by analytical HPLC and ESMS, and fractions containing >95% purity by analytical HPLC were pooled and lyophilized (See, FIG. 11).

EXAMPLE 9

Characterization of Cross-linked Human BNP

Figure 12:
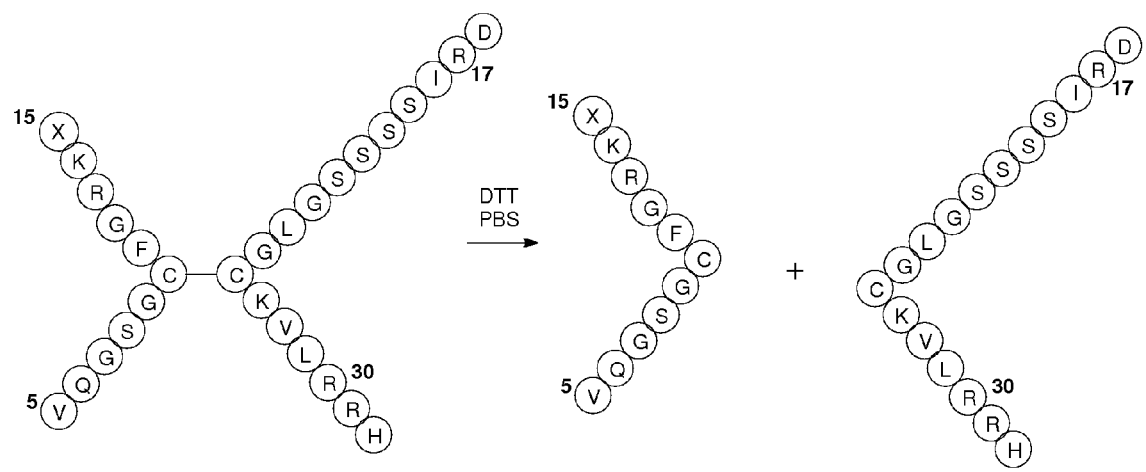
FIG. 12 shows the cleavage of two cross-linked human BNP fragments of a BNP Fragment Composition into individual hBNP fragments and analysis by MALDI demonstrating that the two peptide fragments were cross linked via a disulfide bond. On the left side of the reaction are BNP5-15 (SEQ ID NO: 7) and BNP16-32 (SEQ ID NO: 8) fragments that are cross-linked. On the right side of the reaction are BNP5-15 (SEQ ID NO: 7) and BNP16-32 (SEQ ID NO: 8) fragments that are not cross-linked.

The cross-linked human BNP fragments in Example 8 were shown to be cross-linked at the cysteine at amino acid 10 and the cysteine at amino acid 26 by reducing 0.1 mg of the cross-linked peptide using 0.5 mL of 1 mg/mL dithiothriotol solution in 0.01 M phosphate 150 mM sodium chloride pH 7.2. After reduction, the two human BNP fragments were captured on the Backer Bond Octadecyl ($C_{18}$) resin to remove the salts from the peptide fragments. The resin was washed thoroughly with water. The human BNP fragments were released from the resin using 100 µL of 50% acetonitrile/water in 0.1% TFA. The resin was removed by filtering the solution containing the peptide human BNP fragments. 1 µL of the sample was diluted with 1 µL of cyano-4-hyroxycinnamic acid solution and spotted for MALDI analysis. The solution containing the peptide (human BNP fragments) was analyzed using MALDI to determine the peptide present. It is observed that the peptide present matched the human BNP peptides comprising amino acids 5-15 and amino acids 16-32 on the BNP sequence in Example 8, wherein the residue 15 is a homoserine lactone (instead of methionine) (See, FIG. 12).

EXAMPLE 10

Enzymatic Degradation

Human BNP (1-32) can be enzymatically degraded at specific amino acids by limited proteolysis. Human BNP (1-32) was digested using Arginase C. Arginase C selectively cleaves human BNP (1-32) at arginine amino acids. An enzyme solution containing 1 unit of Arginase C (Worthington Biochemical Corp., Lakewood, N.J.) was prepared pursuant to the manufacturer's directions by dissolving 0.7 mg of Arg-C enzyme in 0.511 mL of 0.1 M Tris buffer, 10 mM $CaCl_2$, 5 mM EDTA, pH 7. A 6.1 mg/mL solution of human BNP (1-32) was prepared by dissolving 10 mg of human BNP (Abbott Laboratories, Abbott Park, Ill.) in 10 mL of 0.1 M Tris buffer pH 7.6, 10 mM $CaCl_2$, 5 mM EDTA. Next, 0.4 mL of Arginase C was added to the human BNP solution and incubated for 30 min. After this, 0.1 mL of 10% aqueous TFA solution was added to quench the reaction. The result was that human BNP was cleaved at position C-terminus at amino acids 29, 30, 16 and 13, thus giving rise to cross-linked human BNP fragments. The cross-linked human BNP fragments included a human BNP fragment comprising amino acids 1-13 cross-linked to a human BNP fragment comprising amino acids 18-30 and a human BNP fragment comprising amino acids 4-13 cross-linked to a human BNP fragment comprising amino acids 18-30. In addition, partial cleavage at the C-terminus of the human BNP fragment comprising amino acids 1-13 at amino acid 3 (lysine) was also observed.

The human BNP fragments described above were obtained after limited proteolysis using an Arginase C digestion peptide (See, FIG. 13) and isolated by reverse phase HPLC (RP-HPLC) purification on Luna C18(2) semipreparative column (Phenomenex, Torrance, Calif.). The sample was injected on Luna C18 (2) 10×250 mm length, that was preequilibrated at 10% actonitrile in 0.1% aqueous TFA, for 15-20 min. The sample was injected and the peptide eluted with a gradient of 10-40% acetonitrile in 0.1% aqueous TFA over 60 min. The peptide elutes around 35-40 min at a flow rate of 5 mL/min. The peptide fractions were analyzed by analytical HPLC and ESMS, and fractions containing >95% purity by analytical HPLC were pooled and lyophilized. The human BNP fragments were identified using electrospray mass spectrometry (API 100, Sciex). The molecular weight determined for the human BNP fragments was consistent with the structures shown in FIG. 13 and the specificity of endoprotease C.

EXAMPLE 11

Cross-linked Peptides as Immunogen

The cross-linked human BNP fragments isolated after chemical degradation/enzymatic degradation as described above in Examples 8 and 10 were used as immunogens to immunize a mouse (the mouse strain was RBF/dnJ, female were purchased from Jackson Laboratories, Bar Harbor, Me.) to produce antibody. The purified cross-linked human BNP fragments were provided as a solution of 1 mg/mL in PBS pH 7.2 for further use as immunogens. 10 µg/mL of cross-linked human BNP fragment was used as an immunogen in Freunds adjuvant, incomplete Freunds adjuvant or Ribi Adjuvant. The cross-linked human BNP fragments are shown in FIGS. 11 and 13.

EXAMPLE 12

Evaluation of the Peptides in Competitive Assay Format

The chemically degraded human BNP fragment described in Example 8 and Example 9 was evaluated in competitive assay format using a microplate luminometer (Berthold Oakridge Tenn.). The paramagnetic microparticles were coated with monoclonal antibody (mAb) 106.3 (A hybridoma cell line expressing monoclonal antibody 106.3 has been deposited with the American Type Culture Collection ("ATCC"), 10801 University Boulevard, Manassas, Va. 20110 and was accorded accession number BH 12044 and is described in U.S. Pat. No. 6,162,902). Anti-human BNP antibody, acridinylated human BNP (1-32) cyclized was used for evaluation.

For the cyclization of human BNP, 220 mg of diAcm (a protecting group for thiols that is deprotected during the cyclization)-hBNP peptide was taken in 120 mL of acetic acid ("AcOH"):$H_2O$ mixture, (4:1 v/v) and 10 mL of 1N HCl was added followed by addition of 150 milligrams of iodine as a solution in 10 mL of methanol ("MeOH"):AcOH (1:1 v/v) (Greg Fields editor, *Methods in Enzymology*, 289:198-221, (1997)). The reaction mixture was stirred for 45 minutes under dark conditions. The reaction mixture was a clear brown solution without any suspended particles. After 45 minutes, the reaction was quenched by adding 10% solution of ascorbic acid (approximately 100 mg of ascorbic acid was added, which is commercially available from Aldrich, Milwaukee, Wis.) solution drop-wise (approximately 10 mL was added) until the solution was clear. The solution was diluted 4 times with water and purified by preparative HPLC. A Phenomenex Luna 10μ, C18(2) 250×50 mm column was used for purification, using a gradient of acetonitrile water 10-40% in 60 minutes. The peptide was collected in fractions as the peak raised and the fractions were checked by HPLC. The fractions with highest purity >98% were pooled and lyophilized. 110 mg of cyclized human BNP peptide was obtained.

The preparation of an anti-human BNP mAb 106.3 microparticle herein in Example 2. The synthetic human BNP (1-32) was extended with residues β-alanine (which was used as a linker) and serine (the oxidation of which gives a reactive aldehyde) (see, Rose, K., *J. Am. Chem. Soc.*, 116:30-33 (1994)). The Ser-β-Ala-Human BNP peptide (1-32) (30 mg) was oxidized with sodium periodate (10 equivalence) for 5 min. The excess sodium periodate was quenched with glycerol (50 μL) to obtain an N-terminal reactive aldehyde with β-Ala linker that was further purified by RP-HPLC purification on a Luna C18 (2) semipreparative column (Phenomenex, Torrance, Calif.). The Glyoxal β-Ala-BNP(1-32) was further coupled with amino-oxy hexylacridinium (Abbott Laboratories, Abbott Park, Ill.) by dissolving the two in 50% aqueous acetonitrile and stirring at room temperature for 4 hrs. The coupled product was isolated by RP-HPLC purification a on Luna C18 (2) semipreparative column (Phenomenex, Torrance, Calif.). The sample was injected on Luna C18 (2) (10×250 mm) column that was preequilibrated at 10% acetonitrile in 0.1% aqueous TFA, for 15-20 min. The sample was injected and the peptide eluted with a gradient of 10-40% acetonitrile in 0.1% aqueous TFA over 60 min. The peptide elutes around 35-40 min at a flow rate of 5 mL/min. The peptide fractions were analyzed by analytical HPLC and ESMS, and fractions containing >95% purity by analytical HPLC were pooled and lyophilized. The acridinylated human BNP reagent (1-32) was used for detection of human BNP in a competitive format.

Figure 14:
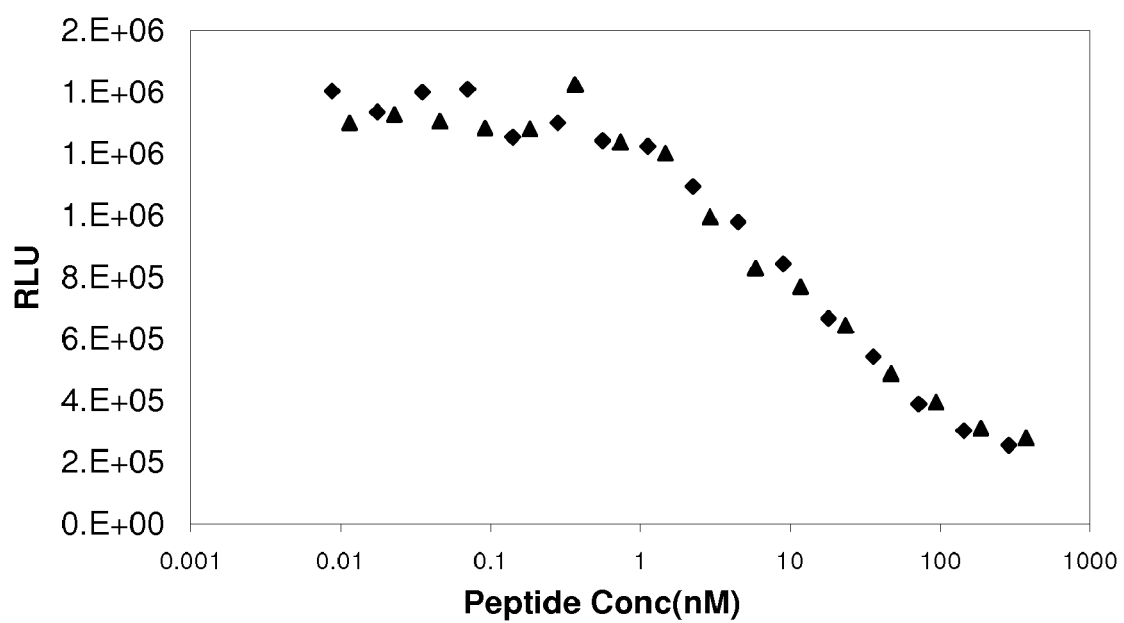
FIG. 14 shows the results of binding of a Human BNP Fragment Composition (defined herein) produced via Arg-C digestion with a monoclonal antibody produced by hybridoma 106.3, using a competitive format with anti-human BNP mAb 106.3 coated microparticles and acridinium-labeled human BNP (1-32). Symbols: ♦ is human BNP 1-32, and ▲ is human BNP fragments cross-linked and obtained using Arg-C (namely, a Human BNP Fragment Composition).
Figure 15:
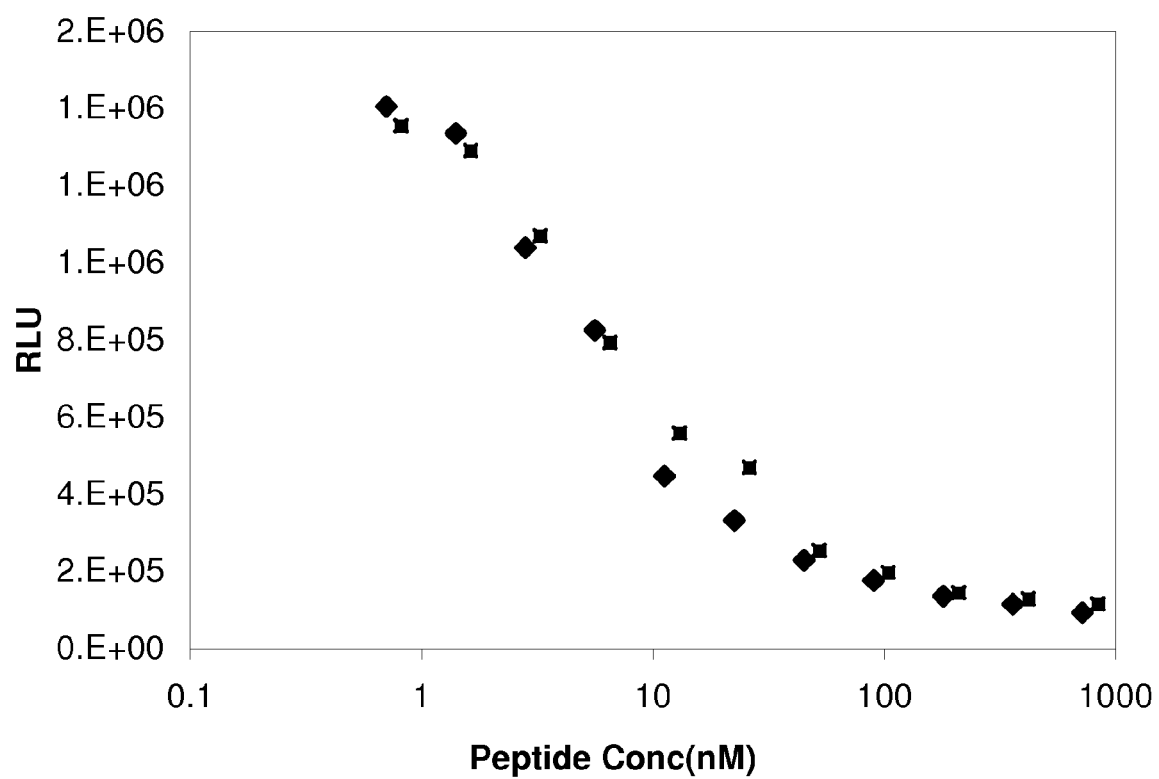
FIG. 15 shows the results of binding of a Human BNP Fragment Composition (defined herein) produced via cyanogen bromide (CNBr) degradation with a monoclonal antibody produced by hybridoma106.3, using a competitive format with anti-human BNP mAb 106.3 coated microparticles and acridinium-labeled human BNP (1-32). Symbols: ♦ is human BNP 1-32, and ■ is human BNP fragment cross-linked and obtained using CNBr (namely, a Human BNP Fragment Composition).

The cross-linked human BNP fragments at various concentrations were incubated with microparticles for 60 min. The unbound human BNP fragments were removed by washing the microparticles. The microparticles were incubated with acridinylated BNP (1-32) for 30 min to occupy the unbound antibody site on the microparticles. The excess acridinylated human BNP (1-32) was washed off repeatedly. The bound acridinylated human BNP (1-32) on the magnetic microparticles were measured using a microplate luminometer (Berthold, Oakridge Tenn.). The results of this binding experiment is illustrated in FIGS. 14 and 15. These Figures show that the cross-linked human BNP fragments produced using either Arginase C (solid triangles, FIG. 14) or cyanogen bromide degradation (solid squares, FIG. 15) are able to competitively bind to the antibody (mAb 106.3) and suppress the binding of the acridinylated human BNP as the concentration of the cross-linked human BNP (solid triangles, both figures) is increased.

EXAMPLE 13

Evaluation of the Peptides in Sandwich Assay Format

The chemically degraded human BNP fragment described in Example 8 was evaluated in competitive assay format using a microtiter plate and chemiluminometer (Berthold, Oakridge Tenn.). The paramagnetic particle was coated with anti-human BNP mAb 106.3 and acridinylated Anti-human BNP mAb BC203 (Abbott Park, Abbott, Ill.) was used for evaluation.

The anti-human BNP mAb 106.3 microparticle was prepared as described in Example 2 above. The acridinylated mAb BC203 was conjugated to acridinium (Abbott Laboratories, Abbott Park, Ill.) using a succinimidyl active ester of acridinium. The acridinylated BC203 mAb was used in the assay during the second incubation to detect the particle bound cross-linked human BNP fragments.

Figure 16:
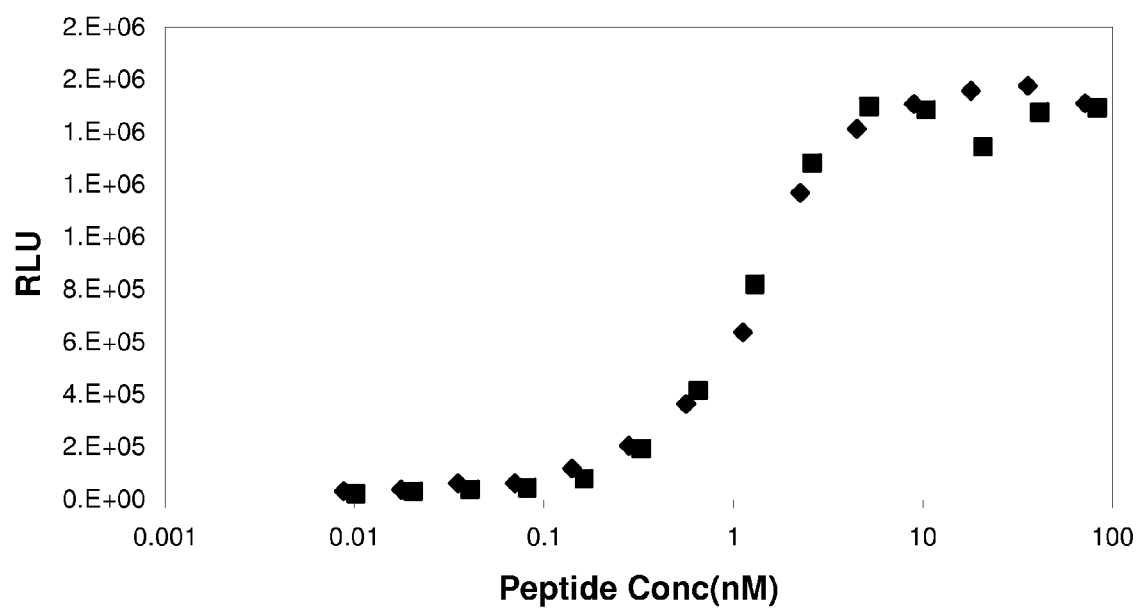
FIG. 16 shows the results of binding of a Human BNP Fragment Composition (defined herein) produced via CNBr degradation to a monoclonal antibody produced by hybridoma BC203 using anti-BNP mAb 106.3 coated microparticles in a sandwich format using an acridinium-labeled monoclonal antibody BC203 conjugate. Symbols: ♦ is human BNP 1-32, and ■ is human BNP fragments cross-linked and obtained using CNBr (namely, a Human BNP Fragment Composition).
Figure 17:
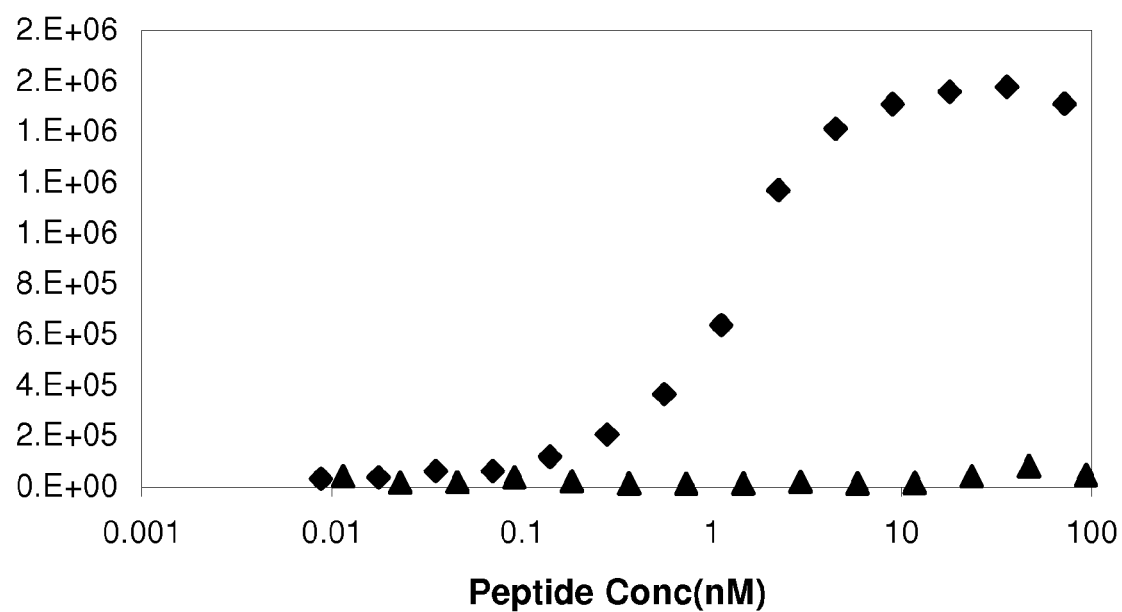
FIG. 17 shows the results of binding of a Human BNP Fragment Composition (defined herein) produced via Arg-C digestion to a monoclonal antibody produced by hybridoma BC203 using anti-BNP mAb 106.3 coated microparticles in a sandwich format using an acridinium-labeled monoclonal antibody BC203 conjugate. Symbols: ♦ is human BNP 1-32, and ▲ is human BNP fragments cross-linked and obtained using Arg C (namely, the Human BNP Fragment Composition).

The mAb 106.3 coated magnetic microparticle (50 μL of 0.1% solids) were incubated with the cross-linked human BNP fragments obtained by chemical degradation or enzymatic degradation (See, Examples 8 or 10) or at various concentrations of cross-linked human BNP (1-32) for 60 min. The unbound cross-linked human BNP (1-32) was washed repeatedly using a magnet to separate the microparticles while the solution was removed and replaced with wash buffer. The 106.3 mAb coated microparticles with the cross-linked human BNP fragments were then incubated with acridinylated Anti-human BNP mAb BC203 antibody, for 60 min. The acridinylated mAb BC 203 binds the cross-linked human BNP fragments already bound to the microparticle. The unbound acridinylated Anti-human BNP mAb BC203 was washed off. The amount of bound Anti-human BNP mAb BC203 directly reads the amount of human BNP fragments bound to the microparticle. The results of these experiments are shown in FIGS. 16 and 17. These FIGS. 16 and 17 show that the cross-linked human BNP fragments produced using either Arginase C (solid triangles, FIG. 17) or cyanogen bromide degradation (solid squares, FIG. 16) are able to competitively bind to the antibody (mAb 106.3) and increase the binding to the acridinium-labeled BC203 conjugate as the concentration of the cross-linked human BNP (solid triangles, both figures) is increased.

EXAMPLE 14

Figure 18:
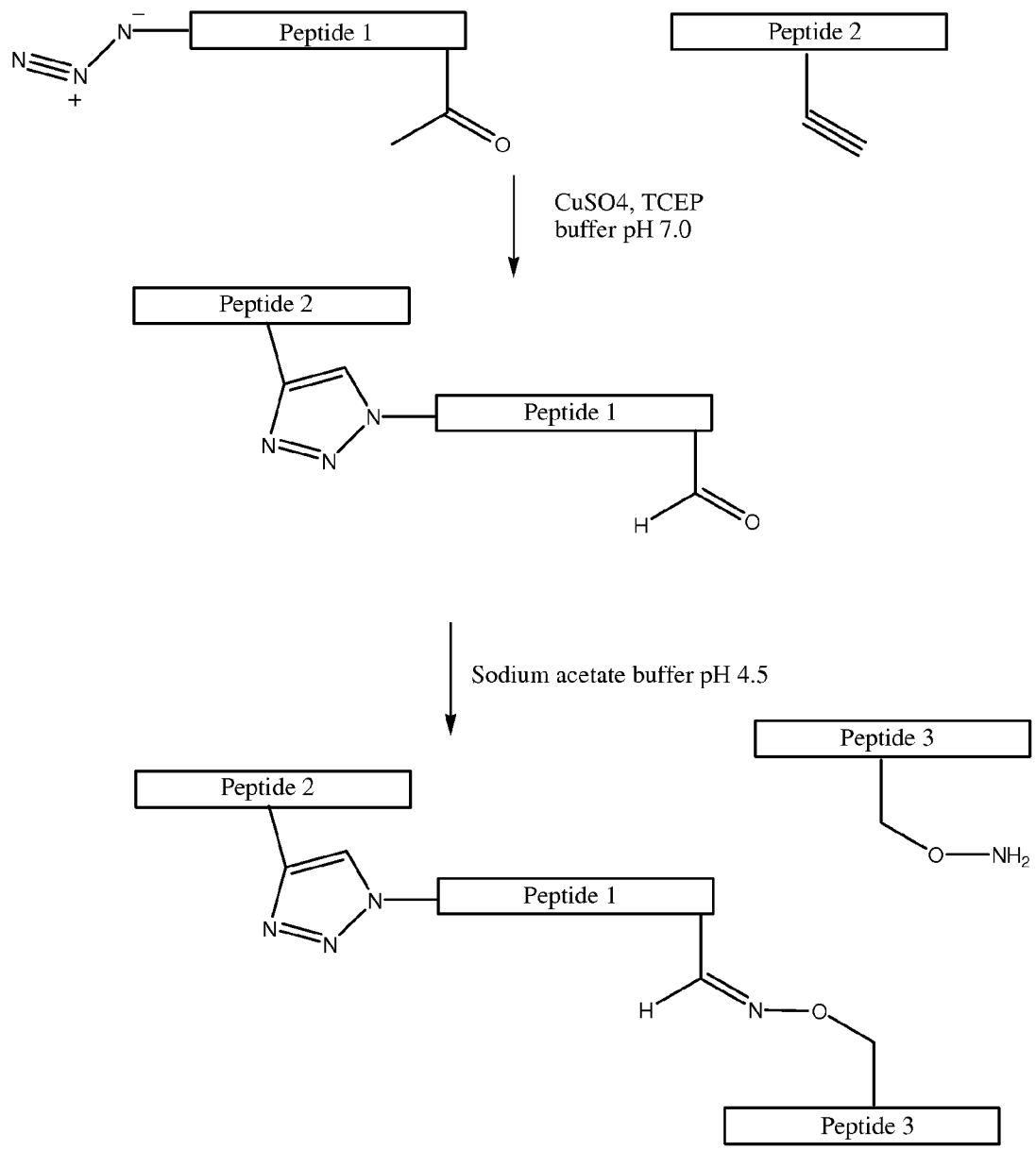
FIG. 18 shows a prophetic example demonstrating how to make a Human BNP Fragment Composition (defined herein) comprising three human BNP fragments. The first human BNP fragment ("Peptide 1") contains two selectively reactive functional groups, e.g., as depicted, an azido group and an aldehyde group. The azido group on Peptide 1 initially reacts with the acetylene group on a second human BNP fragment ("Peptide 2") in the presence of copper sulfate and tricarboxyethylphosphine (hereinafter "TCEP") reducing reagent to form a triazine linkage. The cross-linked Peptide 1 and Peptide 2 further react with a third human BNP fragment ("Peptide 3") containing a $CH_2ONH_2$ group to form an oxime linkage between Peptide 1 and Peptide 3.

Prophetic Example for a Human BNP Fragment Composition Comprising Three Human BNP Fragments This example and FIG. 18 describe how one skilled in the art, using routine techniques, can make a Human BNP Fragment Composition comprising three human BNP fragments. In this example, three human BNP fragments are first prepared to contain selectively reactive functional groups. The selectively reactive functional groups are then reacted to cross-link each of the three human BNP fragments to one another, thus forming a Human BNP Fragment Composition.

In a first human BNP fragment of interest, an amino acid residue carrying a serine on a side chain, such as N-α-Fmoc- N-β-(O-t-butyl-N-t-Boc-L-serinyl)-L-diaminoproionic acid (which is referred to herein as "Fmoc-Dpr(Boc-Ser(tbu))-OH", which is commercially available from EMD Bioscience, Inc., Madison, Wis. The serine in Fmoc-Dpr(Boc-Ser(tbu))-OH is protected via certain protecting groups.), can be introduced into the first human BNP fragment using routine solid phase peptide synthesis, which is well known to those skilled in the art (the first human BNP fragment with the introduced amino acid residue is hereinafter referred to, and is depicted in FIG. 18 as "Peptide 1"). Towards the N-terminus of Peptide 1, another selectively reactive functional group, such as an azido group, can be introduced directly onto the N-terminus of the Peptide 1. After the azido group is introduced, Peptide 1 can be cleaved off the resin (which removes the protecting groups thus resulting in a deprotected diaminopropionic acid ("Dpr")-serine derivative) and purified using routine techniques known in the art. The resulting Dpr-serine derivative can then be oxidized using sodium periodate to release a terminal aldehyde or a glyoxal.

A second human BNP fragment of interest can be prepared by introducing an acetylene group as a side chain derivative by using propargyl-glycine (commercial available from Sigma-Aldrich, St. Louis Mo.), either at the N-terminus or at the C-terminus of the second human BNP fragment using solid phase peptide synthesis (hereinafter referred to and depicted in FIG. 18 as "Peptide 2"). After the solid phase synthesis, Peptide 2 can be cleaved from the resin and purified using routine techniques known in the art.

A third human BNP fragment of interest can be prepared introducing an amino-oxy or hydroxylamine group as a side chain derivative, such as N-α-t-Boc-O-(Fmoc-amino)-L-serine (commercially available from EMD Bioscience, Inc.), at any location on the human BNP fragment, such as, the N-terminus, the C-terminus, or at any location between the N-terminus and the C-terminus, on the human BNP fragment (hereinafter referred to and depicted in FIG. 18 as "Peptide 3") using solid state peptide synthesis. After the solid phase synthesis, Peptide 3 can be cleaved from the resin and purified using routine techniques known in the art.

After preparation of Peptides 1, 2 and 3 as described above, about 2.0 mg/mL or higher of each of Peptide 1 and Peptide 2 can be incubated at room temperature in a phosphate buffer having a pH of about 8.0. This incubation can then be followed by the addition, e.g., of TCEP and $CuSO_4$ (0.5 equivalence) to the mixture of Peptide 1 and Peptide 2. The mixture can then be gently mixed. The mixture is then incubated at room temperature for a period of about 1 hour to about 24 hours. After the incubation, the reaction mixture can then be purified, e.g., using RP-HPLC with an acetonitrile:water gradient employing 0.1% TFA as modifier. The resulting purified Peptide 1-Peptide 2 conjugate can then be further reacted with Peptide 3 (such as in the amount of 1.0 mg/mL or higher) in, e.g., acetonitrile:water mixture or sodium acetate pH 4.5 buffer, to obtain a Human BNP Fragment Composition, namely, a cross-linked Peptide 1-Peptide 2-Peptide 3 conjugate). The resulting Human BNP Fragment Composition can then be purified, such as by using RP-HPLC purification. Of course, variations on this scheme using the teachings provided herein would be well within the ordinary skill of one working in this discipline.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composition comprising: at least two human brain natriuretic peptide (BNP) fragments, wherein each of the human BNP fragments of said composition is cross-linked to at least one of the other human BNP fragments of said composition, wherein said composition comprises a first human BNP fragment and a second human BNP fragment, and wherein the first human BNP fragment has an amino acid sequence consisting of amino acid residues selected from the group consisting of residues 1-13, 1-17, 3-13 and 3-17 of human BNP, and the second human BNP fragment has an amino acid sequence consisting of residues 18-30 or 18-32 of human BNP.

2. The composition of claim 1, wherein the first human BNP fragment and second human BNP fragment are cross-linked at a cysteine residue contained within the first human BNP fragment and the second human BNP fragment.

3. An immunogen comprising a composition of claim 1.

4. The composition of claim 1, wherein the first human BNP fragment consists of residues 3-17 of human BNP and the second human BNP fragment consists of residues 18-30 of human BNP.

5. The composition of claim 1, wherein the first human BNP fragment consists of residues 1-13 of human BNP and the second human BNP fragment consists of residues 18-30 of human BNP.

6. The composition of claim 1, wherein the first human BNP fragment consists of residues 3-13 of human BNP and the second human BNP fragment consists of residues 18-30 of human BNP.

7. The immunogen of claim 3, further comprising a carrier or diluent.

8. The immunogen of claim 7, wherein the carrier or diluent is a sterile liquid selected from the group consisting of selected from the group consisting of water and oil.

9. The immunogen of claim 8, wherein the oil is selected from the group consisting of petroleum, animal, vegetable, peanut, soybean, mineral, and synthetic.

10. The immunogen of claim 8, wherein the carrier or diluent further comprises a substance selected from the group consisting of a surfactant, adjuvant, excipient, and stabilizer.

* * * * *

SEQUENCE LISTING

```
<160> NUMBER OF SEQ ID NOS: 10

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
```

```
                35                  40                  45
Gly Val Trp Lys Ser Arg Glu Val Ala Thr Glu Gly Ile Arg Gly His
        50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 2
<211> LENGTH: 32
<212> TYPE: PRT
<213> ORGANISM: Homo sapiens

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

<210> SEQ ID NO 3
<211> LENGTH: 6
<212> TYPE: PRT
<213> ORGANISM: Homo sapiens

<400> SEQUENCE: 3

Lys Val Leu Arg Arg His
1               5

<210> SEQ ID NO 4
<211> LENGTH: 28
<212> TYPE: PRT
<213> ORGANISM: Artificial Sequence
<220> FEATURE:
<223> OTHER INFORMATION: BNP3-30

<400> SEQUENCE: 4

Lys Met Val Gln Gly Ser Gly Cys Phe Gly Arg Lys Met Asp Arg Ile
1               5                   10                  15

Ser Ser Ser Ser Gly Leu Gly Cys Lys Val Leu Arg
                20                  25

<210> SEQ ID NO 5
<211> LENGTH: 15
<212> TYPE: PRT
<213> ORGANISM: Artificial Sequence
<220> FEATURE:
<223> OTHER INFORMATION: BNP3-30X-1

<400> SEQUENCE: 5

Lys Met Val Gln Gly Ser Gly Cys Phe Gly Arg Lys Met Asp Arg
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: BNP3-30x-2

<400> SEQUENCE: 6

Ile Ser Ser Ser Ser Gly Leu Gly Cys Lys Val Leu Arg
1               5                   10
```

```
<210> SEQ ID NO 7
<211> LENGTH: 11
<212> TYPE: PRT
<213> ORGANISM: Artificial Sequence
<220> FEATURE:
<223> OTHER INFORMATION: 5-15
<220> FEATURE:
<221> NAME/KEY: Xaa
<222> LOCATION: (11)..(11)
<223> OTHER INFORMATION: Xaa is homoserine lactone

<400> SEQUENCE: 7

Val Gln Gly Ser Gly Cys Phe Gly Arg Lys Xaa
1               5                   10

<210> SEQ ID NO 8
<211> LENGTH: 17
<212> TYPE: PRT
<213> ORGANISM: Artificial Sequence
<220> FEATURE:
<223> OTHER INFORMATION: BNP16-32

<400> SEQUENCE: 8

Asp Arg Ile Ser Ser Ser Ser Gly Leu Gly Cys Lys Val Leu Arg Arg
1               5                   10                  15

His

<210> SEQ ID NO 9
<211> LENGTH: 13
<212> TYPE: PRT
<213> ORGANISM: Artificial Sequence
<220> FEATURE:
<223> OTHER INFORMATION: BNP1-13

<400> SEQUENCE: 9

Ser Pro Lys Met Val Gln Gly Ser Gly Cys Phe Gly Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: BNP4-13

<400> SEQUENCE: 10

Met Val Gln Gly Ser Gly Cys Phe Gly Arg
1               5                   10
```